(12) United States Patent
Ikeda et al.

(10) Patent No.: US 11,344,233 B2
(45) Date of Patent: May 31, 2022

(54) HEMOGLOBIN QUANTIFICATION DEVICE, HEMOGLOBIN QUANTIFICATION METHOD, HEMOGLOBIN QUANTIFICATION PROGRAM, AND SURGICAL ASSISTANCE DEVICE

(71) Applicant: Tetsuo Ikeda, Fukuoka (JP)

(72) Inventors: Tetsuo Ikeda, Fukuoka (JP); Hajime Nagahara, Osaka (JP); Eiji Oki, Fukuoka (JP); Ryosuke Tsutsumi, Fukuoka (JP); Makoto Ohsaki, Fukuoka (JP)

(73) Assignee: Tetsuo Ikeda, Fukuoka (JP)

( * ) Notice: Subject to any disclaimer, the term of this patent is extended or adjusted under 35 U.S.C. 154(b) by 245 days.

(21) Appl. No.: 16/499,505

(22) PCT Filed: Mar. 30, 2018

(86) PCT No.: PCT/JP2018/013763
§ 371 (c)(1),
(2) Date: Dec. 18, 2019

(87) PCT Pub. No.: WO2018/181953
PCT Pub. Date: Oct. 4, 2018

(65) Prior Publication Data
US 2020/0383615 A1    Dec. 10, 2020

(30) Foreign Application Priority Data
Mar. 31, 2017    (JP) .................................. 2017-071837

(51) Int. Cl.
*A61B 5/1455*    (2006.01)
*A61B 5/145*    (2006.01)
*A61B 5/00*    (2006.01)

(52) U.S. Cl.
CPC ........ *A61B 5/14546* (2013.01); *A61B 5/1455* (2013.01); *A61B 5/14551* (2013.01); *A61B 5/7425* (2013.01)

(58) Field of Classification Search
CPC .............. A61B 5/1455; A61B 5/14551; A61B 5/14552; A61B 5/14546; A61B 5/1459; A61B 5/742; A61B 5/7425
See application file for complete search history.

(56) References Cited

U.S. PATENT DOCUMENTS 4,914,512 A * 4/1990 Sekiguchi .............. A61B 1/042
                                                          348/453
10,426,325 B2 * 10/2019 Chiba ................... A61B 1/0638
(Continued)

FOREIGN PATENT DOCUMENTS

JP    H03-170866 A    7/1991
JP    2011-200572 A    11/2010
(Continued)

OTHER PUBLICATIONS

WIPO, International Search Report for PCT Patent Application No. PCT/JP2018/013763, dated Jun. 19, 2018.
(Continued)

*Primary Examiner* — Chu Chuan Liu

(57) ABSTRACT

PROBLEMS The present invention provides the hemoglobin quantifying apparatus which is capable of clearly quantifying the oxygen metabolic state of biological tissue by calculating and quantifying the hemoglobin amount of biological tissue in a non-contact and non-invasive manner.
SOLUTION The present invention provides the light receiver unit 2 for receiving any two narrow wavelength band components and white components having reflection characteristics different according to the oxygen saturation of hemoglobin, which are reflected from the biological tissue a, and the hemoglobin amount calculation unit 8 for
(Continued)

calculating the hemoglobin amount based on the light components in the two narrow wavelength bands obtained from the received light components, and the hemoglobin amount calculation unit 8 for correcting the light components in the two narrow wavelength bands based on the blue and green components to calculate the hemoglobin amount.

9 Claims, 18 Drawing Sheets

(56) References Cited

U.S. PATENT DOCUMENTS

| | | | | |
|---|---|---|---|---|
| 2011/0077462 | A1* | 3/2011 | Saitou | A61B 1/063 |
| | | | | 600/109 |
| 2011/0237915 | A1* | 9/2011 | Yamaguchi | A61B 5/14551 |
| | | | | 600/339 |
| 2014/0012113 | A1* | 1/2014 | Kaku | A61B 5/1459 |
| | | | | 600/339 |
| 2018/0020903 | A1 | 1/2018 | Saito | |

FOREIGN PATENT DOCUMENTS

| | | |
|---|---|---|
| JP | 2015-150186 A | 8/2015 |
| WO | 2014/132742 A1 | 9/2014 |
| WO | 2016/158276 A1 | 10/2016 |

OTHER PUBLICATIONS

WIPO, Written Opinion for PCT Patent Application No. PCT/JP2018/013763, dated Jun. 19, 2018.

* cited by examiner

FIG 3
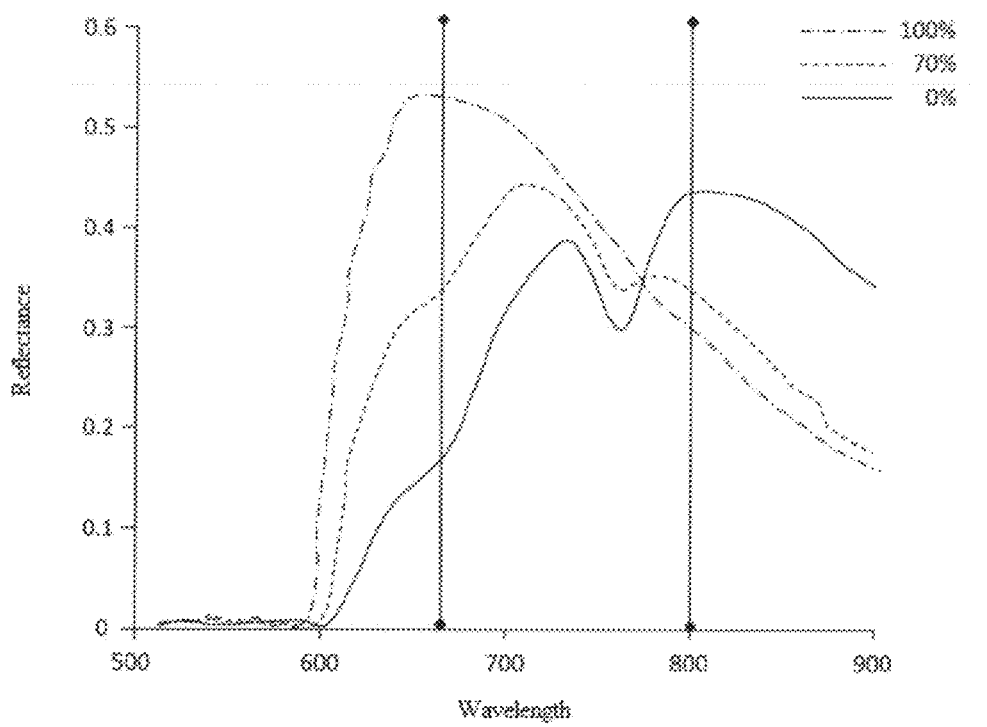
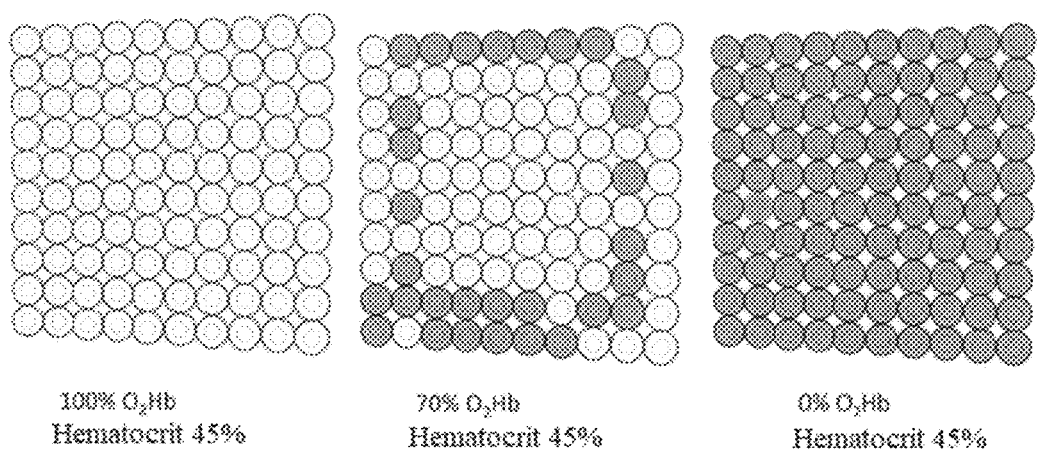
100% O₂Hb
Hematocrit 45%
70% O₂Hb
Hematocrit 45%
0% O₂Hb
Hematocrit 45%

FIG 5
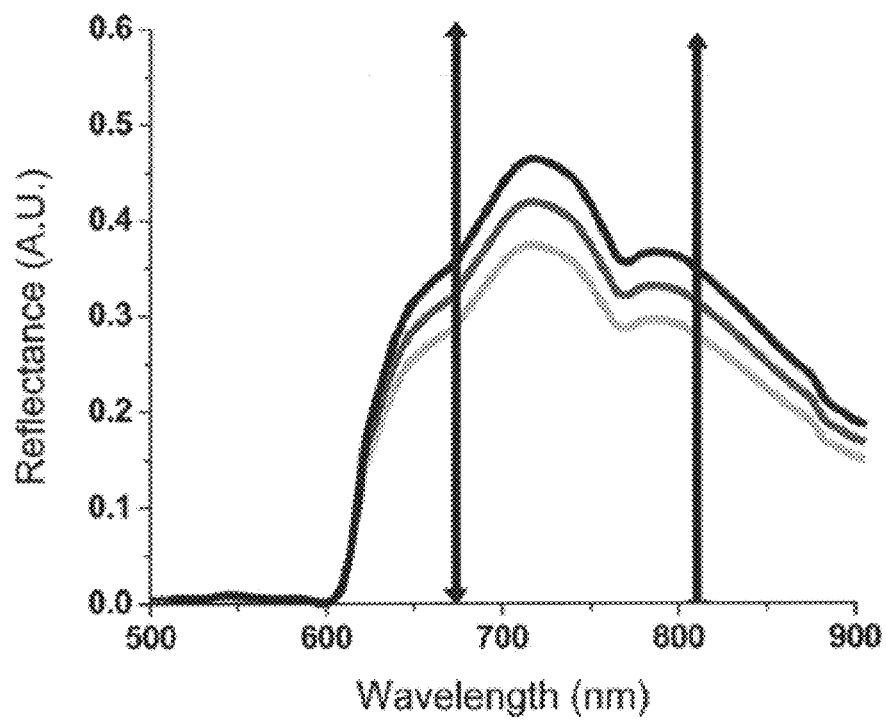
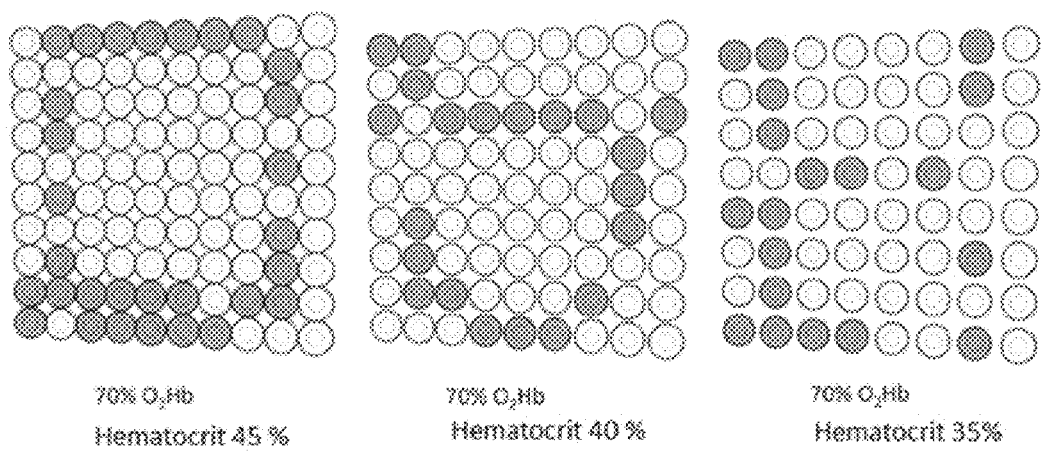
70% O₂Hb
Hematocrit 45 %
70% O₂Hb
Hematocrit 40 %
70% O₂Hb
Hematocrit 35%

FIG 8
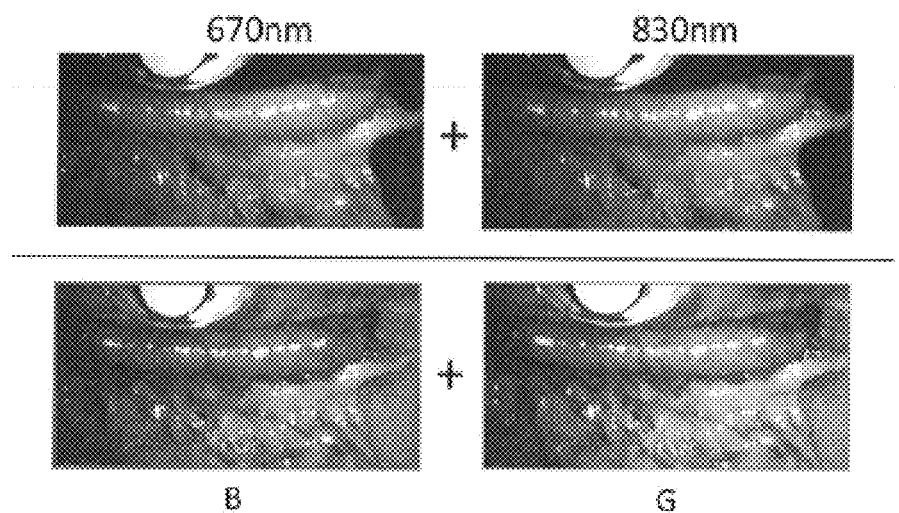
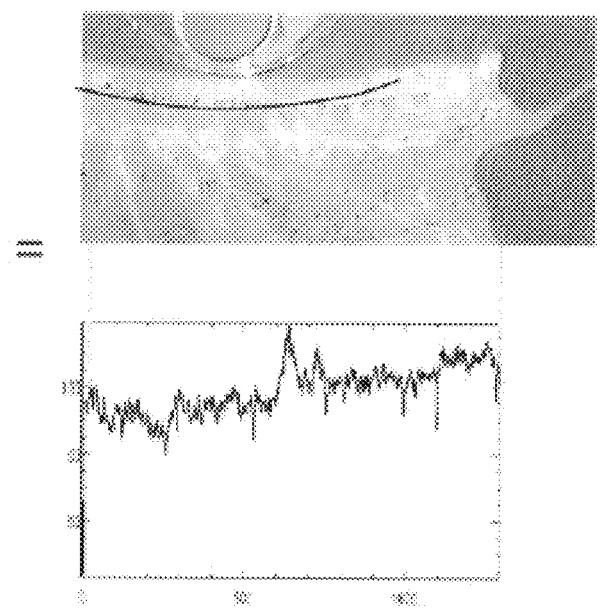

HEMOGLOBIN QUANTIFICATION DEVICE, HEMOGLOBIN QUANTIFICATION METHOD, HEMOGLOBIN QUANTIFICATION PROGRAM, AND SURGICAL ASSISTANCE DEVICE

TECHNICAL FIELD

The present invention relates to a hemoglobin quantifying apparatus for quantifying the oxygen saturation of hemoglobin and the amount of hemoglobin.

BACKGROUND ART

In recent years, advanced and delicate surgical manipulations are required. The needs for surgical navigation techniques has increased rapidly. Surgical navigation assists surgery by processing images obtained before or during surgery on a computer for real-time positional relationship of a surgical field in the course of surgery. However, the current state of navigation is that it does not exceed the planning of a treatment based on the three-dimensional positional relationship between a lesion and a vessel and information sharing thereof (simulation). It is desired to develop a navigation device which can accurately image the state of a biological tissue during an operation and can make an appropriate judgment.

In particular, pulse oximeters for measuring oxygen saturation in blood are widely used as devices capable of non-invasively measuring the oxygen saturation of living organisms in medical fields worldwide. The wavelength band of 650 nm to 1000 nm, in which the absorption of oxyhemoglobin and water is minimized, is a region in which light is difficult to be absorbed by a living body. It is called a "window of a living body" and is used in the above-mentioned pulse oximeters. The pulse oximeter irradiates the skin with near-infrared light, and detects the light that has passed through and scattered through the biological tissue and returned to the skin surface. The pulse oximeter performs measurement by sandwiching the measurement point between a light source and a sensor.

However, a currently popular device such as the pulse oximeter is a device for measuring the oxygen saturation at one point of the living body and reflecting the function of the lungs or the heart of the whole body. (1) The devices measure two-dimensional information of time and oxygen saturation. The positional information is not included in the two dimensional information. The two dimensional information only reflects the cardiopulmonary function of the living body and does not reflect the oxygen metabolism of the tissue. (2) It is not intuitive because only numerical data can be obtained instead of imaging. (3) Since transmitted light or scattered light is used, it is necessary to close the projector and the sensor in the living body locus so as to sandwich the target site. There is a problem that the contact device becomes a spatial obstruction during the procedure including the operation. It disturbs the operation. The tissue damage by the contact of the device is caused.

In connection with above problems, the following techniques are disclosed. According to the technique disclosed in Patent Document 1, the light source device 13 of the electronic endoscope system 10 includes a white light source 30, a semiconductor light source unit 31, and a rotary filter 34. The white light source 30 constantly emits white light BB. The specimen is irradiated with blue narrow band light Nb from the semiconductor light source unit 31 and G color light separated by the rotary filter 34 alternately. The reflection image of blue narrow band light Nb and the reflection image of G color light are alternately imaged. The image data Nb obtained at the time of imaging of the reflection image of blue narrow band light Nb is normalized by the image data G obtained at the time of imaging of reflection image of G color light in order to obtain a signal ratio of Nb/G. A first oxygen saturation image which is an oxygen saturation image of blood hemoglobin can be made based on a color table 65a in which the signal ratio of Nb/G and color information are associated with each other, and a signal ration of Nb/G.

The technique disclosed in Patent Document 2 is a method for measuring the oxygen saturation of hemoglobin in blood based on the intensity of reflected light by irradiating light from the light emitting source into blood with the light emitting source outputting different wavelengths of light, and driving each of the light emitting sources by first and second AC signals having at least two different frequencies to detect the intensity of reflected light from the blood and convert it into an electrical signal, separating the electrical signal into signals containing the frequency components of the first and second AC signals, respectively, and demodulating the signals in synchronization with the first and second AC signals, removing the frequency components of the first or second AC signals by the demodulated signals, respectively, and calculating the oxygen saturation of the hemoglobin blood based on the first and second reflected light intensity signals.

PRIOR-ART DOCUMENT

Patent Document
Patent Document 1 WO 2014/132742 A1
Patent Document 2: Japanese Patent Application Laid-Open No. 3-170866

SUMMARY OF THE INVENTION

Problems to be Solved by the Invention

If the change of tissue can be evaluated by two indices of the hemoglobin oxygen saturation and the total hemoglobin amount in the tissue, it becomes possible to accurately and specifically judge the state of the tissue. For example, with respect to tumor diagnosis, the boundary with normal tissue can be clearly delineated because the tumor is different in oxygen metabolism even though the shape is the same, and it is possible to determine in real time where the tumor is present in the normal native tissue. In the conventional methods, for example, a contrast agent is injected into a blood vessel, then a radiographic image is taken, or a part is extracted and diagnosed pathologically. The real-time determination is useful as a navigation of a treatment such as confirmation of the presence of a tumor and determination of a resection range.

Further, for example, if there is a change in ischemia or congestion in the same organ, oxygen saturation or blood volume in the tissue increases or decreases. The content of hemoglobin is also different between different tissues, and oxygenated hemoglobin in tissues is reduced in malignant tumors with high oxygen consumption. Total hemoglobin levels in inflamed tissue increase when cytokines enrich blood flow. By knowing both the hemoglobin oxygen saturation level and the total hemoglobin amount in the tissue in this way, it is possible to know not only the tissue blood flow but also various information such as the evaluation of the boundary and the activity of the tissue.

However, although the techniques disclosed in Patent Documents 1 and 2 can quantify the oxygen saturation of hemoglobin, the techniques cannot quantify the total hemoglobin amount. Therefore, these techniques have a problem that a more detailed diagnosis cannot be performed.

The present invention provides a hemoglobin quantifying apparatus which is capable of clearly quantifying the oxygen metabolic state of biological tissue by calculating and quantifying the hemoglobin amount of biological tissue in a non-contact and non-invasive manner.

Means for Solving the Problems

The hemoglobin quantifying apparatus according to the present invention comprises: a component acquiring means for acquiring light components of arbitrary two narrow wavelength bands having reflection characteristics different according to the oxygen saturation of hemoglobin and white components reflected from biological tissue, and a hemoglobin amount calculating means for calculating the hemoglobin amount based on the light components in the two narrow wavelength bands, wherein the hemoglobin amount calculating means calculates the hemoglobin amount by correcting the light components in the two narrow wavelength bands based on the blue component and the green component to calculate the hemoglobin amount.

As described above, the hemoglobin quantifying apparatus according to the present invention includes the component acquiring means for obtaining any two components of narrow wavelength bands and white components having reflection characteristics different according to the oxygen saturation of hemoglobin, which are reflected light from biological tissue, and the hemoglobin amount calculating means for calculating the hemoglobin amount based on the light components in the two narrow wavelength bands, and the hemoglobin amount calculating means for correcting the light components in the two narrow wavelength bands based on the blue component and the green component to calculate the hemoglobin amount, so that it is possible to quantify the hemoglobin amount that cannot be measured by a pulse oximeter and similar devices. It is possible to obtain an effect that the hemoglobin amount can be used for more accurate diagnosis of tissue oxygen metabolism.

The hemoglobin quantifying apparatus according to the present invention includes oxygen saturation calculating means for calculating the oxygen saturation of the hemoglobin based on the ratio of the light components in the two narrow wavelength bands.

As described above, in the hemoglobin quantifying apparatus according to the present invention, since the hemoglobin oxygen saturation can be calculated in addition to the hemoglobin amount of the tissue, it is possible to clearly quantify the oxygen metabolism of tissue based on the respective values.

In addition, by calculating the hemoglobin amount and the hemoglobin oxygen saturation, it is possible to evaluate the blood flow of organs, diagnose tumors and determine the invasion range, and diagnose the degree and range of inflammation.

In the hemoglobin quantifying apparatus according to the present invention, the oxygen saturation calculating means calculates the oxygen saturation based on the oxygen saturation of the pulsating artery during the operation.

As described above, in the hemoglobin quantifying apparatus according to the present invention, since the oxygen saturation calculating means calculates the oxygen saturation based on the oxygen saturation of the pulsating artery during the operation, it is possible to accurately calculate and quantify the hemoglobin oxygen saturation by using the arterial blood sufficiently oxygenated with reaching the limit and the state in which the hemoglobin oxygen saturation is surely high as a reference.

The hemoglobin quantifying apparatus according to the present invention includes display control means for switching and displaying the hemoglobin amount calculated by the hemoglobin amount calculating means and the oxygen saturation calculated by the oxygen saturation calculating means.

As described above, in the hemoglobin quantifying apparatus according to the present invention, since the hemoglobin amount calculated by the hemoglobin amount calculating means and the oxygen saturation calculated by the oxygen saturation calculating means are provided with the display control means for switching and displaying, respectively, the hemoglobin amount and the hemoglobin oxygen saturation can be confirmed in real time by images, and an effect that the hemoglobin amount and the hemoglobin oxygen saturation can be used as a surgical navigation can be obtained.

In the hemoglobin quantifying apparatus according to the present invention, the hemoglobin amount calculating means calculates a light amount indicating a hemoglobin amount by correcting based on the sum value of the light components in the two narrow wavelength bands, the blue component, and the green component.

As described above, in the hemoglobin quantifying apparatus according to the present invention, since the hemoglobin amount calculating means calculates the amount of light indicating the amount of hemoglobin by correcting based on the sum value of the light components in the two narrow wavelength bands, the blue component and the green component the shading caused by the shape of target tissues, illuminance unevenness and illumination unevenness can be corrected by using the blue component and the green component which do not participate in the reflection characteristic of hemoglobin The effect that the amount of hemoglobin can be accurately calculated is obtained.

The treatment support apparatus according to the present invention is a treatment support apparatus using the hemoglobin quantifying apparatus described above, and comprises: an image generating means for generating an image from the light component of the hemoglobin amount calculated by the hemoglobin amount calculating means; an image generating means for generating an image based on the light component of the oxygen saturation of the hemoglobin calculated by the oxygen saturation calculating means; a display control means for displaying each generated image on a display; an anastomosis site specifying means for specifying the anastomosis site in the displayed image based on the operation of the user; and a determining means for determining whether the anastomosis is permitted based on the hemoglobin amount and the oxygen saturation of the hemoglobin at the specified anastomosis site.

As described above, the treatment support apparatus according to the present invention generates an image from the light component of the hemoglobin amount, generates an image based on the light component of the oxygen saturation of the hemoglobin, displays each generated image on the display, specifies the anastomosis point in the displayed image based on the operation of the user, and makes a determination as to whether the anastomosis is permitted based on the hemoglobin amount and the oxygen saturation of the hemoglobin at the specified anastomosis point, and thus has the effect that it becomes possible to objectively present and determine the position suitable as the anastomosis point not only by the judgment of the user (physician), but also as a numerical value. The calculation of the hemoglobin amount and the hemoglobin oxygen saturation makes it possible to evaluate the blood flow of organs, to diagnose tumors and determine the invasion range, to diagnose the degree and range of inflammation, in addition to the possibility of anastomosis.

BRIEF DESCRIPTION OF THE DRAWINGS

FIG. 3 is a graph showing reflection characteristics for each wavelength band according to hemoglobin oxygen saturation.

FIG. 5 shows the change in total hemoglobin at 70% oxygen saturation.

FIG. 8 is a diagram showing an image obtained by quantifying the total hemoglobin amount.

DETAILED DESCRIPTION OF THE INVENTION

Figure 1:
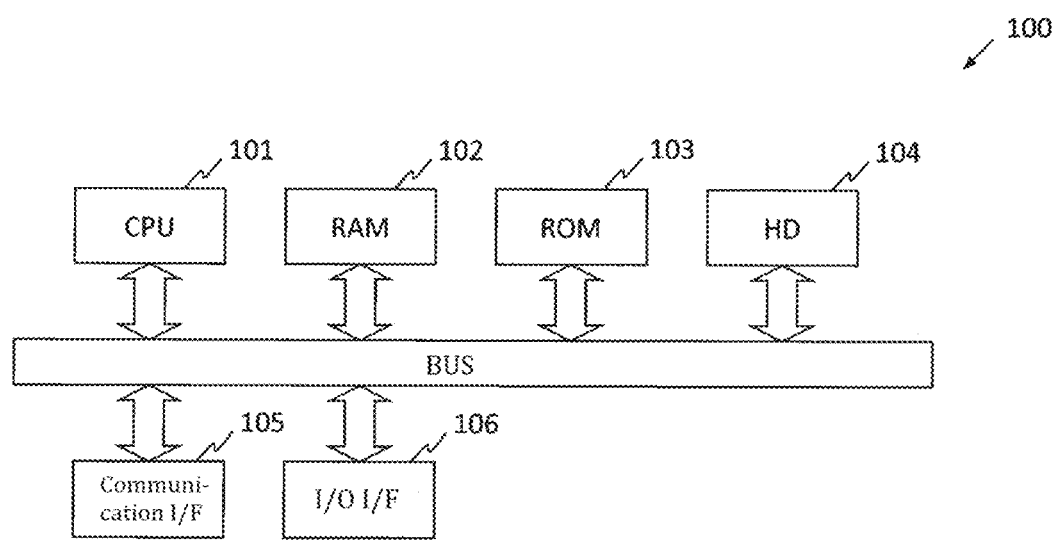
FIG. 1 is a hardware configuration diagram of the hemoglobin quantifying apparatus according to the first embodiment.

Embodiments of the present invention will be described below. In addition, the same elements are denoted by the same reference numerals throughout the present embodiment.

First Embodiment of the Invention

The hemoglobin quantifying apparatus according to the present embodiment will be described with reference to FIGS. 1 to 10. The hemoglobin quantifying apparatus according to the present embodiment acquires the reflected light at the time of imaging of the biological tissue as the first wavelength band component, the second wavelength band component, and the white component, then calculates the oxygen saturation of the hemoglobin and the amount of the hemoglobin by using the received reflected light. In addition, an image is generated based on each of the calculated values and displayed on the display in real time, thereby functioning as a surgical navigation.

FIG. 1 is a hardware configuration diagram of the hemoglobin quantifying apparatus according to the present embodiment. The computer 100 of the hemoglobin quantifying apparatus 1 includes CPU101, RAM102, ROM103, hard disk 104, communication I/F105, and input/output I/F106. The ROM103 and the hard disk104 store an operating system, programs, databases, etc. The programs are read out to the RAM102 and executed by the CPU101 as required.

The communication I/F105 is an interface for performing communication between devices. The input/output I/F106 is an interface for accepting input from input devices such as touch panels, keyboards, mouse devices, etc., and for outputting data to printers, displays, etc. The input/output I/F106 can be connected to drives corresponding to magneto-optical disks, removable disks such as CD-R, DVD-R, etc. as required. Each processing unit is connected via a bus and exchanges information. The configuration of the hardware described above is merely an example, and can be changed as necessary.

Figure 2:
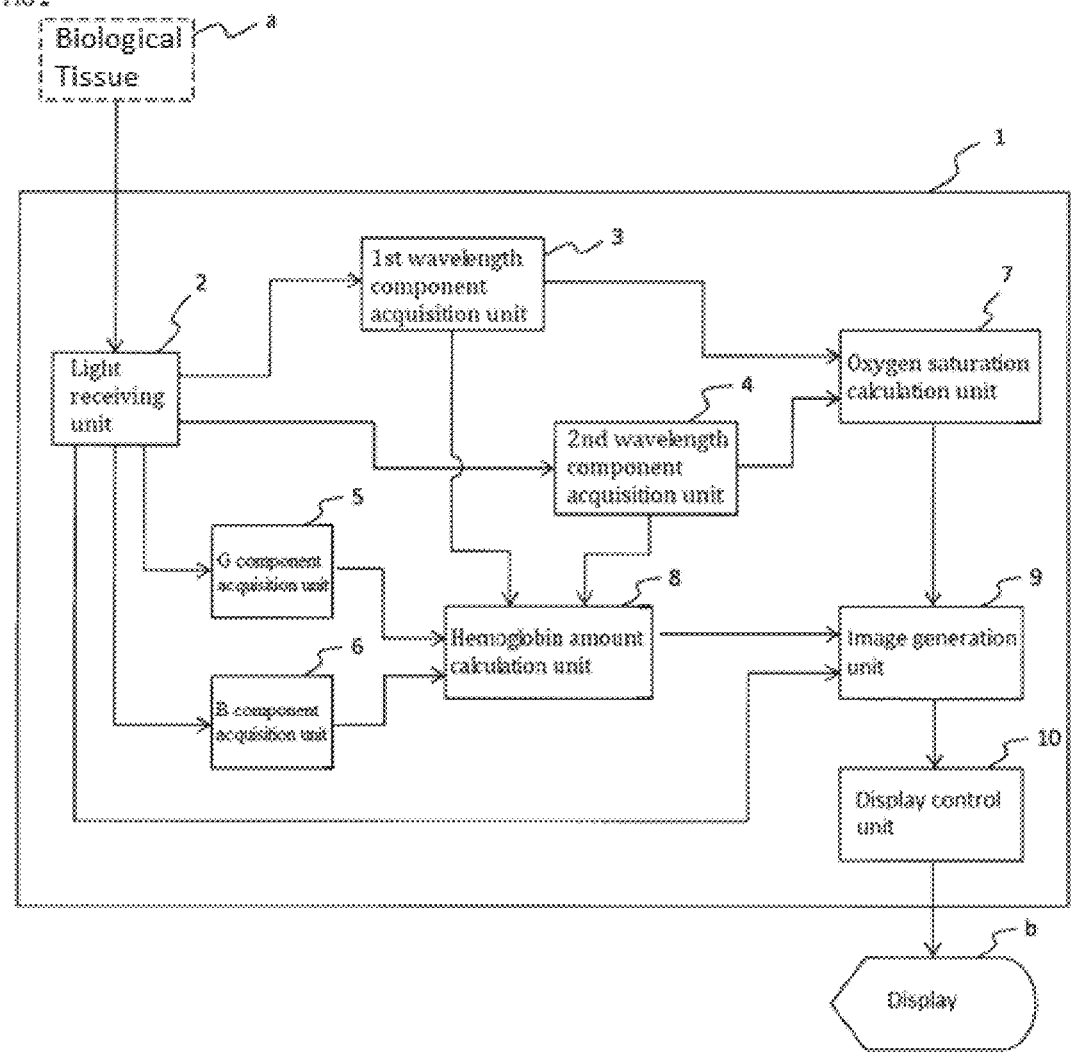
FIG. 2 is a functional block diagram showing the configuration of the hemoglobin quantifying apparatus according to the first embodiment.

FIG. 2 is a functional block diagram showing the configuration of the hemoglobin quantifying apparatus according to the present embodiment. The hemoglobin quantifying apparatus 1 includes a light receiver unit 2 for receiving reflected light reflected from a biological tissue a, a first wavelength component acquisition unit 3 for acquiring a light component in a first wavelength band from the received reflected light, a second wavelength component acquisition unit 4 for acquiring a light component in a second wavelength band from the received reflected light, a G component acquisition unit 5 for acquiring a green color component of a white color component in the received reflected light, a B component acquisition unit 6 for acquiring a blue color component of a white color component in the received reflected light, an oxygen saturation calculation unit 7 for calculating hemoglobin oxygen saturation based on the light component acquired by the first wavelength component acquisition unit 3 and the light component acquired by the second wavelength component acquisition unit 4 and a total hemoglobin amount calculation unit 8 for calculating total hemoglobin amount based on the light component acquired by the first wavelength component acquisition unit 3, a light component acquired by the second wavelength component acquisition unit 4, a light component acquired by the G component acquisition unit 5, and a light component acquired by the B component acquisition unit 6.

The apparatus includes an image generation unit 9 that generates an image from the light component of the hemoglobin oxygen saturation calculated by the oxygen saturation calculation unit 7 and generates an image from the light component of the total hemoglobin amount calculated by the hemoglobin amount calculation unit 8, and a display control unit 10 that switches and displays the generated image of the hemoglobin oxygen saturation and the total hemoglobin amount image on the display b based on the operation of the user.

Hemoglobin to be quantified in the present embodiment will be described. Hemoglobin accounts for the majority of red blood cells. It is composed of a heme pigment and a globin protein. Hemoglobin in erythrocytes has the property of binding to oxygen molecules and is responsible for the transport of oxygen from the lungs to the whole body. Oxygenated hemoglobin carries oxygen to the tissues of the body, and instead receives carbon dioxide and returns to the lungs as reduced hemoglobin, which in turn combines with oxygen to carry oxygen to the tissues of the body. Since the reflection characteristic of each spectrum differs between the oxyhemoglobin and the reduced hemoglobin, the color tone of the whole hemoglobin changes with the ratio of the oxyhemoglobin and the reduced hemoglobin. For example, when the oxygen saturation is high, the oxyhemoglobin absorbs near-infrared light (wavelength: 830 nm) well, so that a large amount of red light is detected. When the oxygen saturation is low, the reduced hemoglobin absorbs red light (wavelength: 670 nm) and thus a large amount of near-infrared light is detected. Therefore, according to the reflection characteristic of hemoglobin, arterial blood having high oxygen saturation has a bright red color, and venous blood having low oxygen saturation has a dark brown color.

The hemoglobin quantifying apparatus according to the present embodiment quantifies hemoglobin by utilizing the reflection characteristics of oxygenated hemoglobin and reduced hemoglobin. The first wavelength band and the second wavelength band described above are arbitrarily two narrow wavelength bands having different reflection characteristics according to the oxygen saturation of hemoglobin, for example, the first wavelength band is a wavelength band of 670 nm and the second wavelength band is a wavelength band of 830 nm. FIG. 3 shows the reflection characteristics for each wavelength band according to the hemoglobin oxygen saturation. As shown in FIG. 3, when the hemoglobin oxygen saturation is 100%, the light component gradually increases from the wavelength of about 600 nm to the wavelength band of about 670 nm. It becomes a peak value at 670 nm. The light component gradually decreases as the wavelength becomes longer. On the other hand, when the hemoglobin oxygen saturation is 0%, the light component gradually increases from the wavelength of about 600 nm to the wavelength band of about 670 nm. The maximum peak appears at 830 nm after the peak appears once around 730 nm. The light component gradually decreases as the wavelength becomes longer. When the hemoglobin oxygen saturation is 70%, the light component gradually increases from a wavelength of about 600 nm to a wavelength band of about 670 nm. The maximum peak appears around 710 nm, and the light component gradually decreases as the wavelength becomes longer. As described above, since the reflectance of each spectrum of hemoglobin differs depending on the ratio of the oxygenated hemoglobin and the reduced hemoglobin, the shape of the graph showing the reflection characteristics of each wavelength band differs. That is, the hemoglobin has the same graph shape when the ratio of the oxygenated hemoglobin and the reduced hemoglobin is the same.

Here, as can be seen from FIG. 3, in the wavelength band of 670 nm, as the hemoglobin oxygen saturation is higher, the component of the reflected light is larger, and the component of the reflected light decreases significantly in accordance with the decrease in the hemoglobin oxygen saturation. On the other hand, in the wavelength band of 830 nm, as the hemoglobin oxygen saturation is higher, the component of the reflected light is smaller, and the component of the reflected light is slightly increased in accordance with the decrease in the hemoglobin oxygen saturation. That is, in the wavelength band of 670 nm and the wavelength band of 830 nm, the relationship between the hemoglobin oxygen saturation and the reflected light component has a complementary relationship, and changes in accordance with each relationship. In the present embodiment, as will be described later, it is possible to calculate the hemoglobin oxygen saturation and the hemoglobin amount by utilizing the correlation of the reflection characteristics between these two wavelengths.

Figure 4:
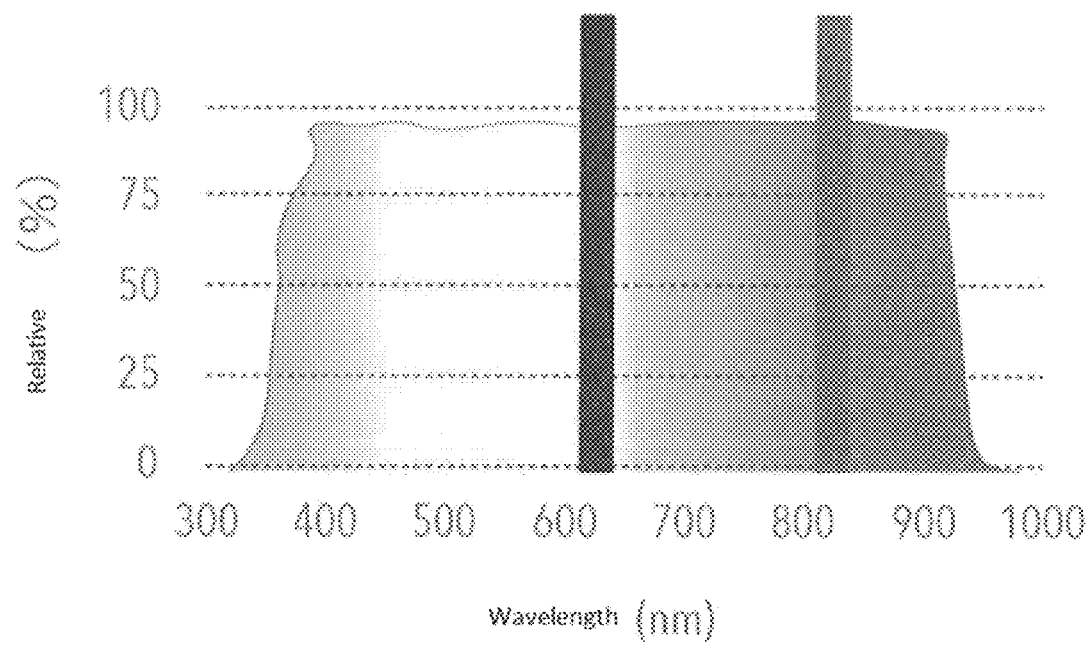
FIG. 4 shows the spectral characteristics of the active projector.

The light receiver unit 2 is a sensor that receives reflected light of biological tissue, and for example, reflected light when the biological tissue is irradiated with an active light projection type projector is received by the light receiver unit 2. At this time, light generated by the projector having spectral characteristics as shown in FIG. 4 is irradiated to the biological tissue. That is, the biological tissue is irradiated with a lamp having a component uniformly in a wavelength band of about 300 nm to 1000 nm, a lamp having a component in a wavelength band of 670 nm, and a lamp having a component in a wavelength band of 830 nm. This active illumination method is a method of obtaining hyperspectral images by photographing while switching illumination having different spectra, and switching of illumination is electrically controlled similarly to the liquid crystal tunable filter, so that two-dimensional spectroscopic images of targets can be obtained at high speed.

It should be noted that a configuration may be adopted in which only light components in a necessary wavelength band are extracted by filtering without performing irradiation by an active light projection type projector. In the filter method, spectral images can be obtained by installing filters that passes only light in specific wavelength region in front of a sensor such as a CCD camera and taking images.

For the reflected light received by the light receiver unit 2, the first wavelength component acquisition unit 3 that acquires a light component in a wavelength band of 670 nm, the second wavelength component acquisition unit 4 that acquires a light component in a wavelength band of 830 nm, the G component acquisition unit 5 that acquires a green component, and the B component acquisition unit 6 that acquires a blue component.

The processing of the oxygen saturation calculation unit 7 and the hemoglobin amount calculation unit 8 will be described below. The oxygen saturation calculation unit 7 calculates the oxygen saturation in the blood based on the reflectance in the 670 nm wavelength band acquired by the first wavelength component acquisition unit 3 and the reflectance in the 830 nm wavelength band acquired by the second wavelength component acquisition unit 4. The degree of reflection of light by a substance is defined as the reflectance. The amount of reflected light can be measured by using a sensor such as a CCD if the irradiation amount is constant. A substance having a constant reflectance corresponding to a spectrum also has a greater amount of reflected light as the concentration (density) per a constant area of the substance increases. The absorbance of a solution makes it possible to know the concentration of a solute in a liquid by Lambert-Beer's law. In the case of two substances (solutes), the relative concentration of the substance can be known by measuring the reflectance (absorbance) of the substance by applying light of two wavelengths. Therefore, hemoglobin composed of oxygenated hemoglobin and reduced hemoglobin can know the relative concentration of each by applying light of two kinds of wavelengths.

[Equation 1]

$$\text{O}_2 \text{ Saturation} = \frac{\text{O}_2Hb}{\text{O}_2Hb + dHb} = r \times \frac{P_1 R670}{P_1 R830} \quad (1)$$

r is the correlation coefficient, $P_1R670$ is the reflectance at the wavelength of 670 nm at the $P_1$ point, and $P_1R830$ is the reflectance at the wavelength of 830 nm at the $P_1$ point.

It is the amount of reflected light that can actually be measured, not the reflectance. However, the amount of reflected light at the $P_1$ point is obtained by multiplying the amount of irradiated light at the $P_1$ point by the reflectance, as shown in the following equation.

$$P_1 LR670 = LP_1 \times P_1 R670 \quad \text{[Equation 2]}$$

$$P_1 LR830 = LP_1 \times P_1 R830$$

$$\text{O}_2 \text{ Saturation} = \frac{\text{O}_2Hb}{\text{O}_2Hb + dHb} = \frac{P_1 LR670 \times P_1 R670}{P_1 LR830 \times P_1 R830}$$

The $LP_1$ indicates the amount of irradiated light at the $P_1$ point.

If the amount of irradiated light at 670 nm and 830 nm is set to be equal in illumination, the following equations can be obtained.

$$P_1 LR670 = P_1 LR830 \quad \text{[Equation 3]}$$

$$\text{O}_2 \text{ Saturation} = $$

$$\frac{\text{O}_2 Hb}{\text{O}_2 Hb + dHb} = \frac{P_1 LR670 \times P_1 R670}{P_1 LR830 \times P_1 R830} = r \times \frac{P_1 R670}{P_1 R830}$$

Assume that $LP_1R670$ is the amount of irradiation light having a wavelength of 670 nm at the $P_1$ point, and $LP_1R830$ is the amount of irradiation light having a wavelength of 830 nm at the $P_1$ point.

That is, as shown in FIG. 3, the reflected light components of the respective wavelengths (670 nm and 830 nm) differ according to the ratio of the amount of oxyhemoglobin and the amount of reduced hemoglobin, and have a correlation between the respective wavelengths, so that the oxygen saturation in the blood can be calculated by the above equation (1). The ratio of reflected light components between 670 nm and 830 nm reflects the hemoglobin oxygen saturation at some instant in the on-screen position $P_1$. Since this value is calculated by taking the ratio of the two values, it is a numerical value that can cope with changes in the amount of irradiated light over different times and portions. In other words, it is useful for observation over time and comparison with other sites. However, in order to make an absolute evaluation, it is necessary to determine a criterion for unifying the scale of the absolute value (measured value) and the calculated quantitative value. In order to unify the scales of the measured and quantitative values, a factor $K_1$ with the oxygen saturation (R670 nm/R830 nm) of the pulsating arteries as the reference 100 of the maximum value is calculated by using the fact that the whole body is sufficiently oxygenated during the operation. That is, the oxygen saturation is calculated by the following equation.

$$\text{O}_2 \text{ Saturation} = \frac{\text{O}_2 Hb}{\text{O}_2 Hb + dHb} = K_1 \times r \times \frac{P_1 R670}{P_1 R830} = 100 \quad \text{[Equation 4]}$$

$$K_1 = 100 \div r \times \frac{P_1 R670}{P_1 R830}$$

Also in the calculation of the hemoglobin amount by the hemoglobin amount calculation unit 8, as the concentration (density) of the substance per a certain area increases, the amount of reflected light increases. As for the absorbance of the solution, as described above, the relative concentration of the substance can be known by Lambert-Beer's law, and the amount of hemoglobin composed of oxyhemoglobin and reduced hemoglobin can be calculated by applying light of two kinds of wavelengths similarly to the oxygen saturation.

When two substances having different reflection characteristics are present in various proportions, the total concentration can be calculated as follows. FIG. 3 shows that the shape of the graph showing the reflection characteristics differs depending on the relative concentration of the materials having different reflectances, but when the relative concentration is constant and the absolute concentration changes, the absolute value of the graph showing the reflection characteristics changes as it is, as shown in FIG. 5. As the absolute concentration decreases, the reflectivity decreases at all wavelengths. However, since the original reflectance is different, the influence of the relative concentration of oxyhemoglobin and reduced hemoglobin cannot be excluded by only the change of the reflection amount of one wavelength.

Here, the absolute amount of hemoglobin is quantified using the reflection amount at 670 nm where the reflectance increases in proportion to the oxygen-saturation at the $P_1$ point and 830 nm where the reflectance decreases in inverse proportion to the oxygen-saturation. Since the amounts of increase and decrease are originally different between the two wavelengths, it is possible to calculate an absolute amount that is not affected by the relative concentrations of oxygenated hemoglobin and reduced hemoglobin by using the coefficient i in consideration of the widths of increase and decrease at the two wavelengths.

The absolute amount of hemoglobin (Hb amount) in the $P_1$ point can be calculated by the following equation:

$$Hb_{amount} = \text{O}_2 Hb + dHb = rP_1 L(R670 + iR830) \quad \text{[Equation 5]}$$

Here, in calculating the oxygen saturation (relative concentration of oxyhemoglobin and reduced hemoglobin), it was possible to cancel the effect of the irradiation amount of light by taking the ratio of the amount of reflected light of each wavelength. However, it is necessary to correct the influence of the irradiation amount of light, that is, shading caused by unevenness of biological tissue or illumination unevenness, because the ratio cannot be taken in the calculation of the absolute amount. For the correction, the G (green) component and the B (Blue) component are used. These components are not affected by the change of the hemoglobin and are included in the RGB color components simultaneously capturing the light of the same light source.

$$Hb_{amount} = \quad \text{[Equation 6]}$$

$$\text{O}_2 Hb + dHb = r\frac{P_1 L(R670 + iR830)}{P_1 L(B+G)} = r\frac{(R670 + ir830)}{(B+G)}$$

In order to unify the scale of the measured value and the quantitative value even in the absolute amount of hemoglobin, the $(R670+R830)/R(B+G)$ in the pulsating arteries without congestion or ischemia is used as 100 for the calculation of the corrected value $K_2$. This can be shown by the following equations:

$$Hb_{amount} = O_2Hb + dHb = K_2 \times r\frac{(R670 + ir830)}{(B+G)} = 100 \quad \text{[Equation 7]}$$

$$K_2 = 100 \div r\frac{(R670 + ir830)}{(B+G)}$$

By correcting the ratio of R(B+G) in this manner, it is possible to correct shading and quantify the absolute value of hemoglobin.

The image generation unit 9 generates an image by replacing the hemoglobin oxygen saturation and the total hemoglobin amount calculated by the oxygen saturation calculation unit 7 and the hemoglobin amount calculation unit 8 with pixels. The display control unit 10 switches the image indicating the hemoglobin oxygen saturation generated by the image generation unit 9 and the image indicating the total hemoglobin amount in accordance with the operation of the user and displays them on the display b in real time.

Figure 6:
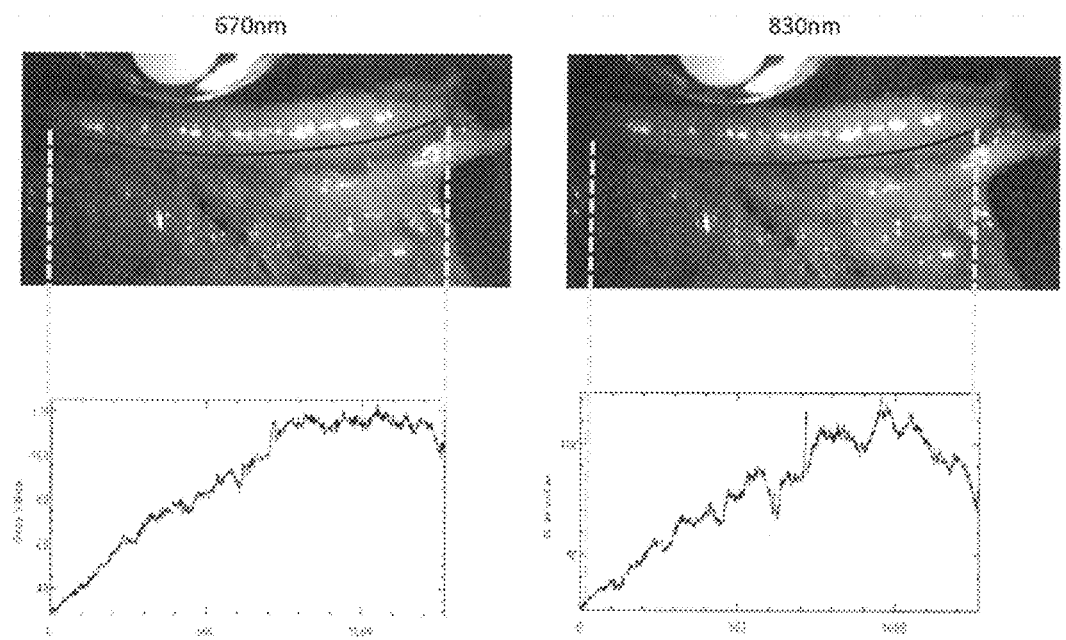
FIG. 6 is a diagram showing an image of biological tissue in a wavelength band of 670 nm and an image of biological tissue in a wavelength band of 830 nm.
Figure 7:
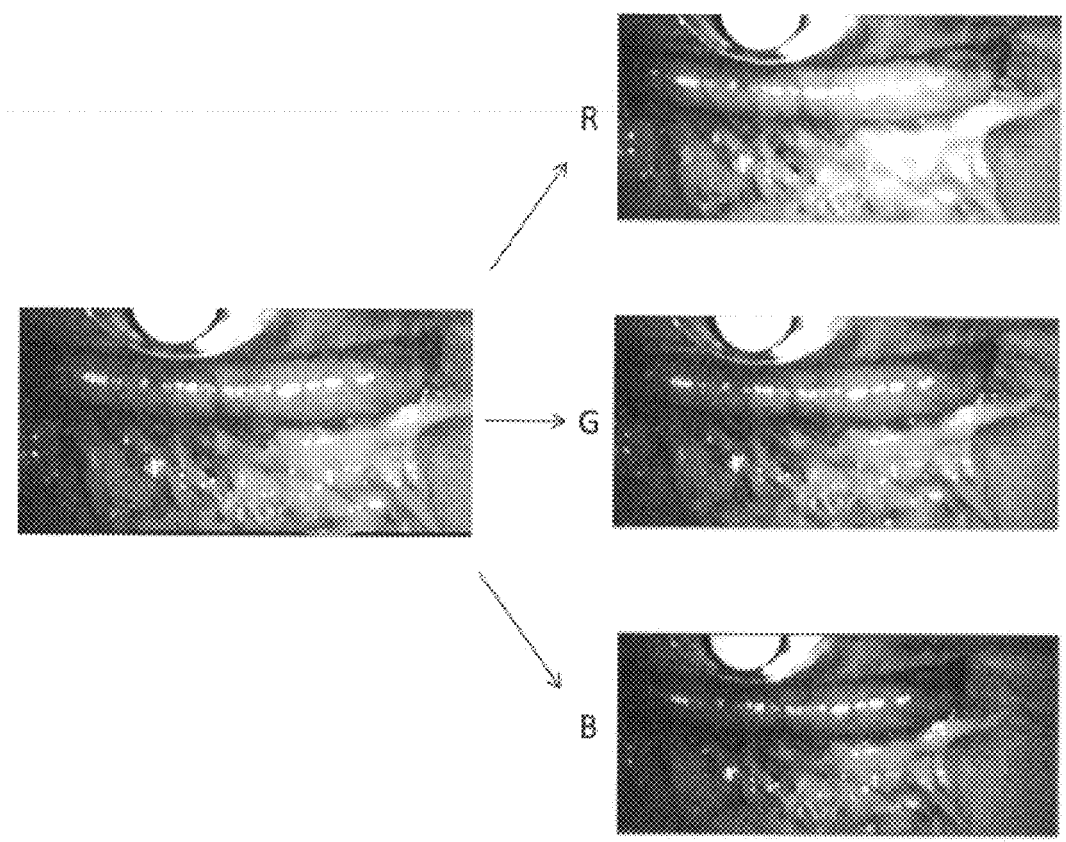
FIG. 7 shows the R, G and B components divided from the color image and displayed for each component.
Figure 9:
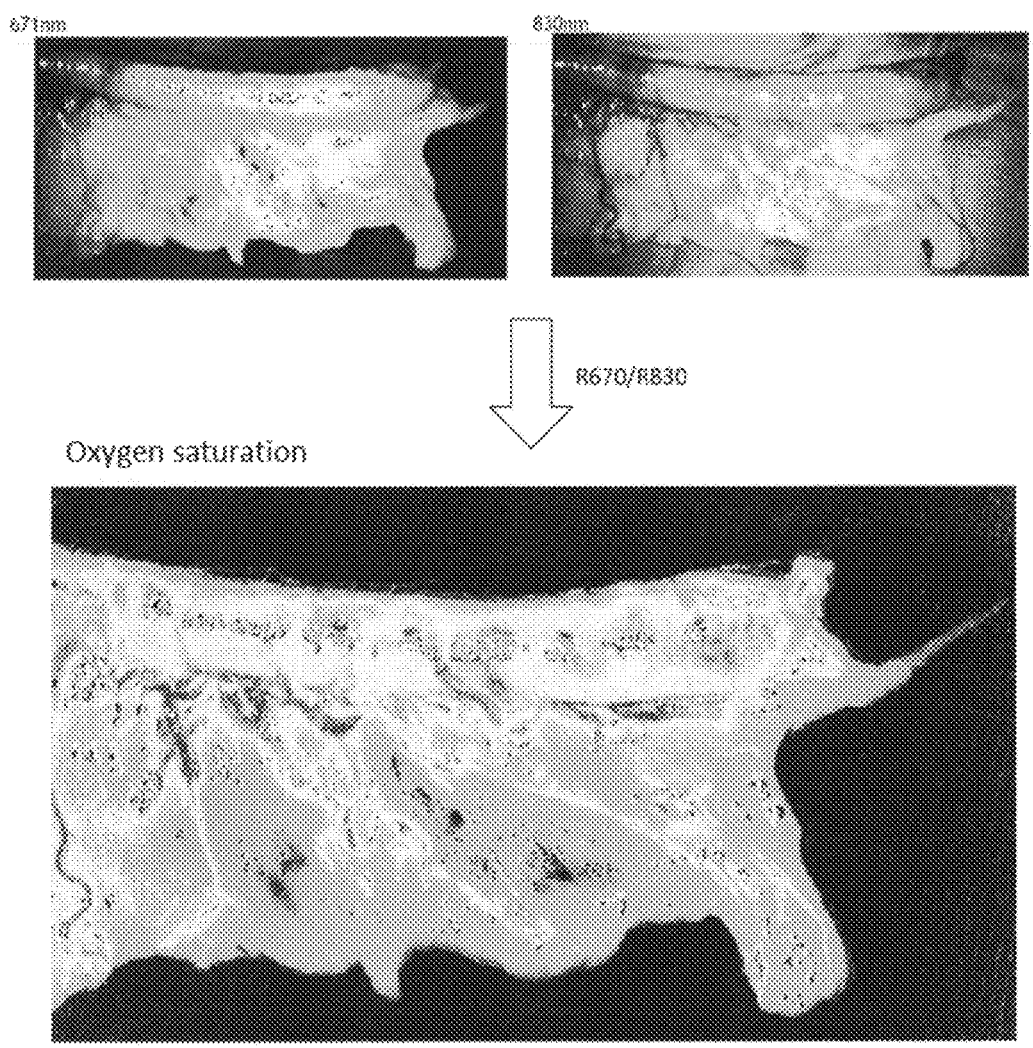
FIG. 9 shows an image of oxygen saturation.

FIGS. 6 to 9 show specific images. FIG. 6 shows an image of biological tissue in the wavelength band of 670 nm and an image of biological tissue in the wavelength band of 830 nm. In FIG. 7, the R component, the G component, and the B component are divided from the color image and displayed for each component. By dividing the added value of the image of each wavelength band in FIG. 6 by the added value of the G component and the B component in FIG. 7, it is possible to generate an image in which the total hemoglobin amount is quantified as shown in FIG. 8. Further, by calculating dividing image ($P_1 670/P_1 830$) of the respective wavelength bands shown in FIG. 6, an image showing oxygen saturation can be generated as shown in FIG. 9. Since the images of FIGS. 8 and 9 are generated individually, they are displayed by switching according to the operation of the user, or they are displayed on the same screen at the same time.

Figure 10:
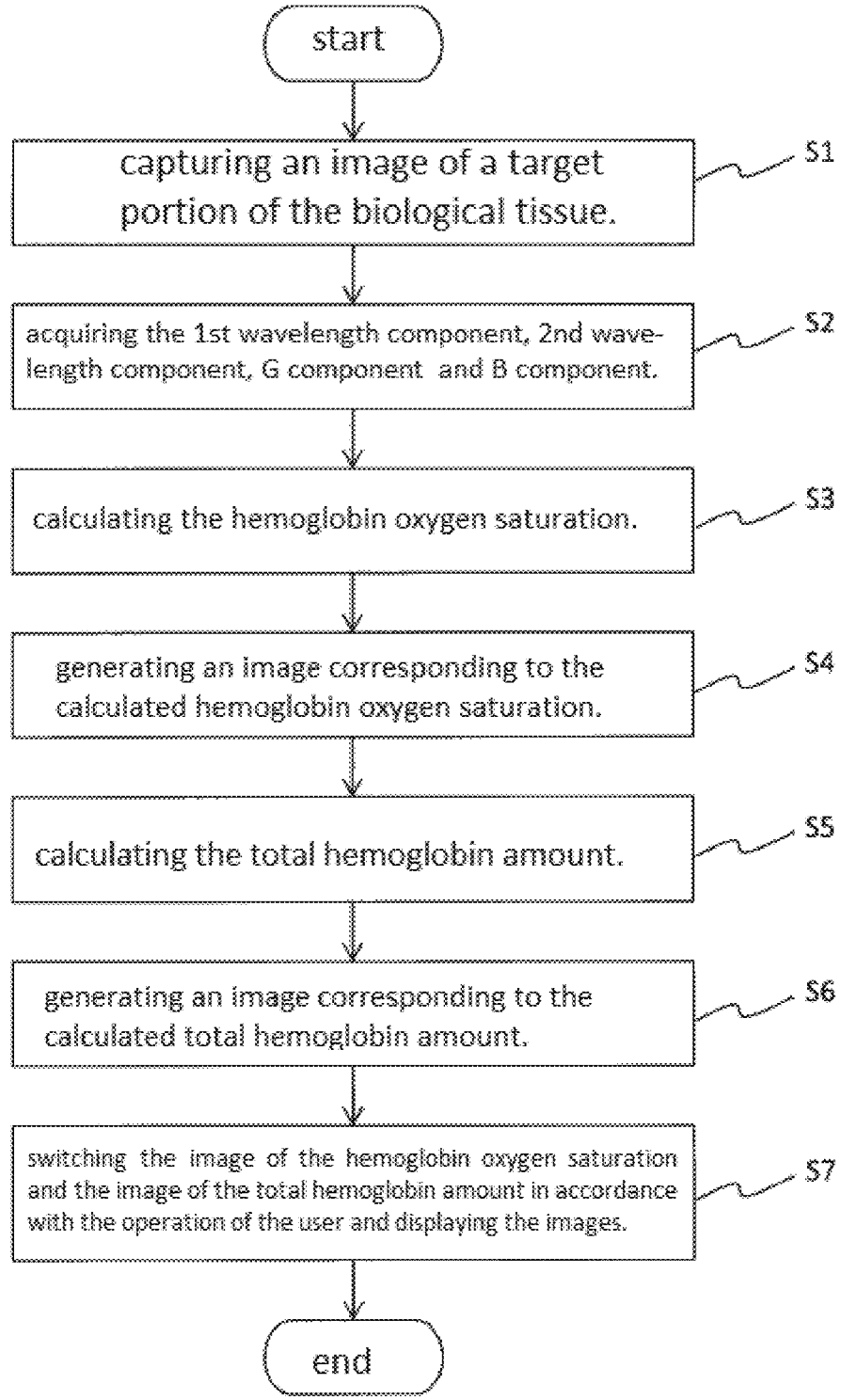
FIG. 10 is a flowchart showing the operation of the hemoglobin quantifying apparatus according to the first embodiment.

Next, the operation of the hemoglobin quantifying apparatus according to the present embodiment will be described. FIG. 10 is a flowchart showing the operation of the hemoglobin quantifying apparatus according to the present embodiment. First, in step S1, the light receiver unit 2 of the camera or the sensor captures an image of a target portion of the biological tissue. The first wavelength component acquisition unit 3 acquires a component of a wavelength band of 670 nm, the second wavelength component acquisition unit 4 acquires a component of a wavelength band of 830 nm, the G component acquisition unit 5 acquires a G component (green component) of RGB, and the B component acquisition unit 6 acquires a B component (blue component) of RGB (S2). In step S3, the oxygen saturation calculation unit 7 calculates the hemoglobin oxygen saturation based on the component of the 670 nm wavelength band acquired by the first wavelength component acquisition unit 3 and the component of the 830 nm wavelength band acquired by the second wavelength component acquisition unit 4. In step S4, the image generation unit 9 generates an image corresponding to the calculated hemoglobin oxygen saturation. In step S5, the hemoglobin amount calculation unit 8 calculates the total hemoglobin amount based on the component of the 670 nm wavelength band acquired by the first wavelength component acquisition unit 3, the component of the 830 nm wavelength band acquired by the second wavelength component acquisition unit 4, the G component of the RGB acquired by the G component acquisition unit 5, and the B component of the RGB acquired by the B component acquisition unit 6. In step S6, the image generation unit 9 generates an image corresponding to the calculated total hemoglobin amount. In step S7, the display control unit 10 switches the image of the hemoglobin oxygen saturation and the image of the total hemoglobin amount in accordance with the operation of the user, or simultaneously displays the images on the same screen, and ends the processing.

As described above, in the hemoglobin quantifying apparatus according to the present embodiment, the hemoglobin amount calculation unit 8 for calculating the hemoglobin amount based on the light components in the two narrow wavelength bands is provided, and the hemoglobin amount calculation unit 8 corrects the light components in the two narrow wavelength bands based on the blue component and the green component to calculate the hemoglobin amount, so that it is possible to obtain the total hemoglobin amount that cannot be measured by conventional devices such as a pulse oximeter, and it is possible to use the total hemoglobin amount for more accurate diagnosis.

In addition, since the hemoglobin oxygen saturation can be calculated in addition to the total hemoglobin amount, accurate and detailed diagnosis based on the respective values is possible.

Further, since the oxygen saturation is calculated based on the oxygen saturation of the artery during the operation, it is possible to accurately calculate the hemoglobin oxygen saturation by using the state in which the hemoglobin oxygen saturation is surely high as a reference.

Furthermore, since the hemoglobin amount and the oxygen saturation are respectively switched and displayed, it becomes possible to confirm the total hemoglobin amount and the hemoglobin oxygen saturation in real time by an image, and it can be used as a surgical navigation.

Furthermore, by using the blue component and the green component which are not involved in the reflection characteristic of the hemoglobin, it is possible to remove the information on the components unnecessary for the calculation, and it is possible to accurately calculate the total hemoglobin amount.

Furthermore, by calculating the hemoglobin amount and the hemoglobin oxygen saturation, it becomes possible to use them for evaluation of blood flow of organs, diagnosis of tumors and determination of the invasion range, and diagnosis of the degree and range of inflammation, etc.

Second Embodiment of the Invention

The hemoglobin quantifying apparatus according to the present embodiment will be described with reference to FIG. 11. The hemoglobin quantifying apparatus according to the present embodiment has a function of preventing flicker that may occur when a biological tissue is irradiated with an active light projection type light projector.

Since the active projectors switch and use projectors of different wavelengths in a short time, flicker occurs. If a flicker occurs when an image is picked up with the naked eye or an ordinary RGB camera, the flicker becomes very disturbing to the user. Although the human eye and the RGB camera have three kinds of color sensitivities, the actual primary color of light is observed by being integrated by the human visual characteristics as shown in the following equation.

$$\begin{pmatrix} X \\ Y \\ Z \end{pmatrix} = \begin{pmatrix} \overline{x_1} & \cdots & \overline{x_{N_b}} \\ \overline{y_1} & \cdots & \overline{y_{N_b}} \\ \overline{z_1} & \cdots & \overline{z_{N_b}} \end{pmatrix} \begin{pmatrix} L_{11}^{w_1} + \ldots + L_{1Nl}^{w_{Nl}} \\ \vdots \\ L_{Nb1}^{w_1} + \ldots + L_{NbN1}^{w_{Nl}} \end{pmatrix}$$ [Equation 8]

That is, the light component of 680 nm which is the first wavelength band or 830 nm which is the second wavelength band can be restored as an image, and in consideration of human visual characteristics, the light combination L of such wavelengths that the change of the observation color due to the switching of the projector is not perceived is obtained by optimization of the above equation, and by configuring the active projector, the multi-spectrum measurement in which the flicker is eliminated becomes possible.

Figure 11:
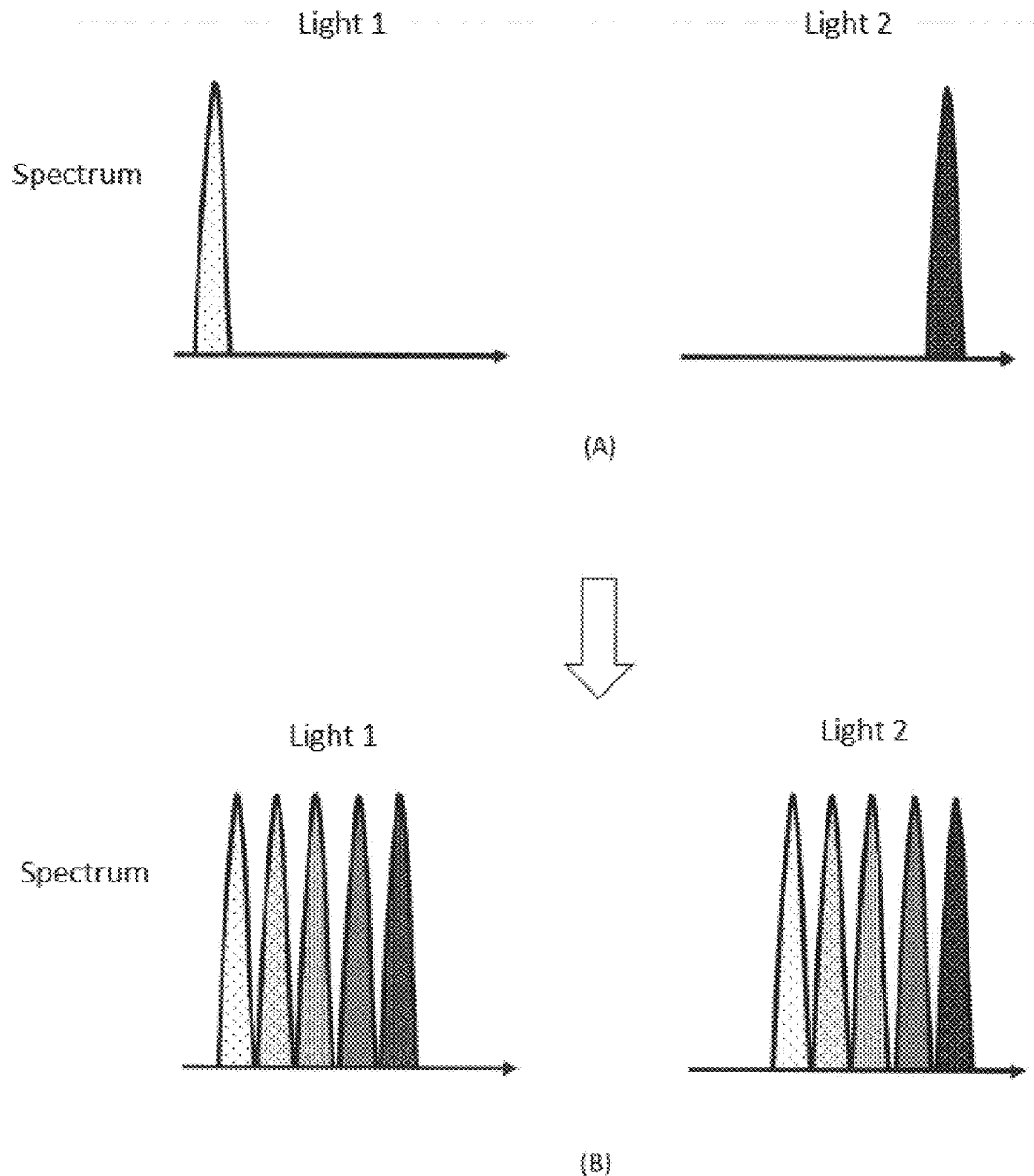
FIG. 11 is a diagram showing an example of a spectrum when flicker is eliminated in the hemoglobin quantifying apparatus according to the second embodiment.

FIG. 11 is a diagram showing an example of a spectrum when flicker is eliminated. As shown in FIG. 11A, when light components (first wavelength band and second wavelength band) in two different wavelength bands are switched and used in the illumination 1 and the illumination 2, flicker occurs. On the other hand, as shown in FIG. 11B, by adding light components of wavelength bands in the vicinity of the respective wavelength bands and other wavelength bands such that the light components of the respective illumination are similar, it is possible to reduce the difference between the light components of the illumination 1 and the light components of the illumination 2 and prevent flicker.

In the above description, the method of eliminating flicker by reducing the difference in light component between the illuminations (projectors) has been described, but in the case of blinking the illumination of a single visible light (e.g., 680 nm), the difference between the case of irradiating and the case of not irradiating the single visible light may be reduced by adding a weak light component in the wavelength band in the vicinity of the visible light to prevent flicker.

As described above, in the hemoglobin quantifying apparatus according to the present embodiment, when light is irradiated by the active light projection type, flicker caused by switching of illumination can be prevented, and the biological tissue can be imaged so as not to interfere with the user.

Third Embodiment of the Invention

A treatment support apparatus using the hemoglobin quantifying apparatus according to the present embodiment will be described with reference to FIGS. 12 and 13. The treatment support apparatus according to the present embodiment determines the anastomosis site based on the oxygen saturation and the hemoglobin amount of the hemoglobin obtained by the hemoglobin quantifying apparatus in each of the embodiments.

Figure 12:
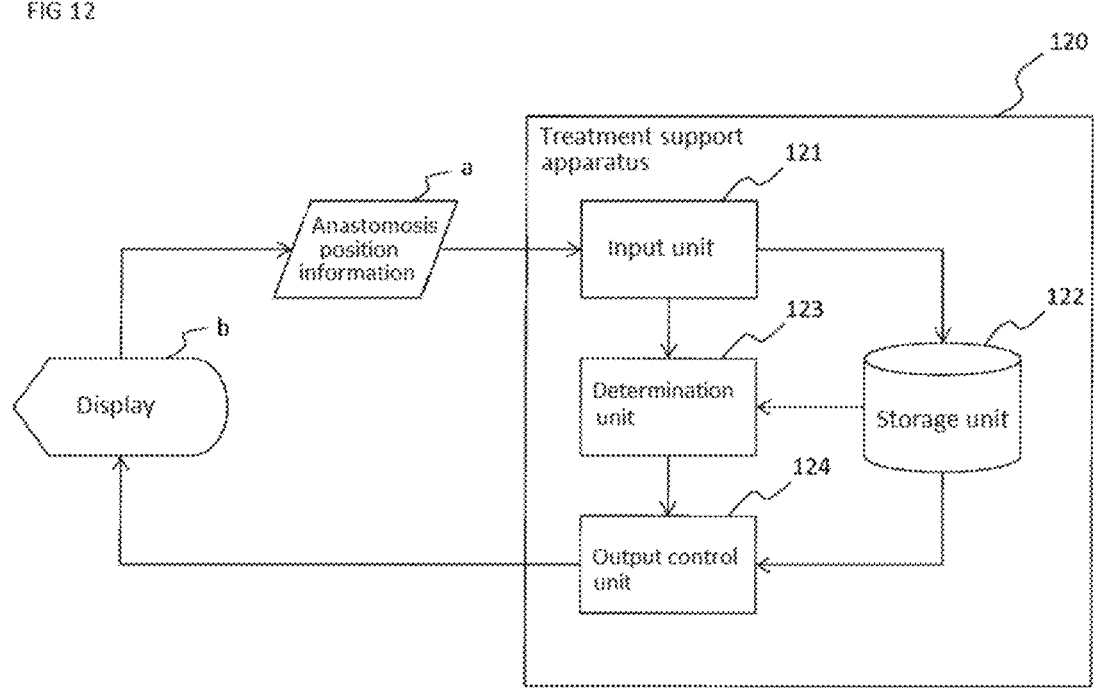
FIG. 12 is a functional block diagram showing a configuration of a treatment support apparatus according to a third embodiment.
Figure 13:
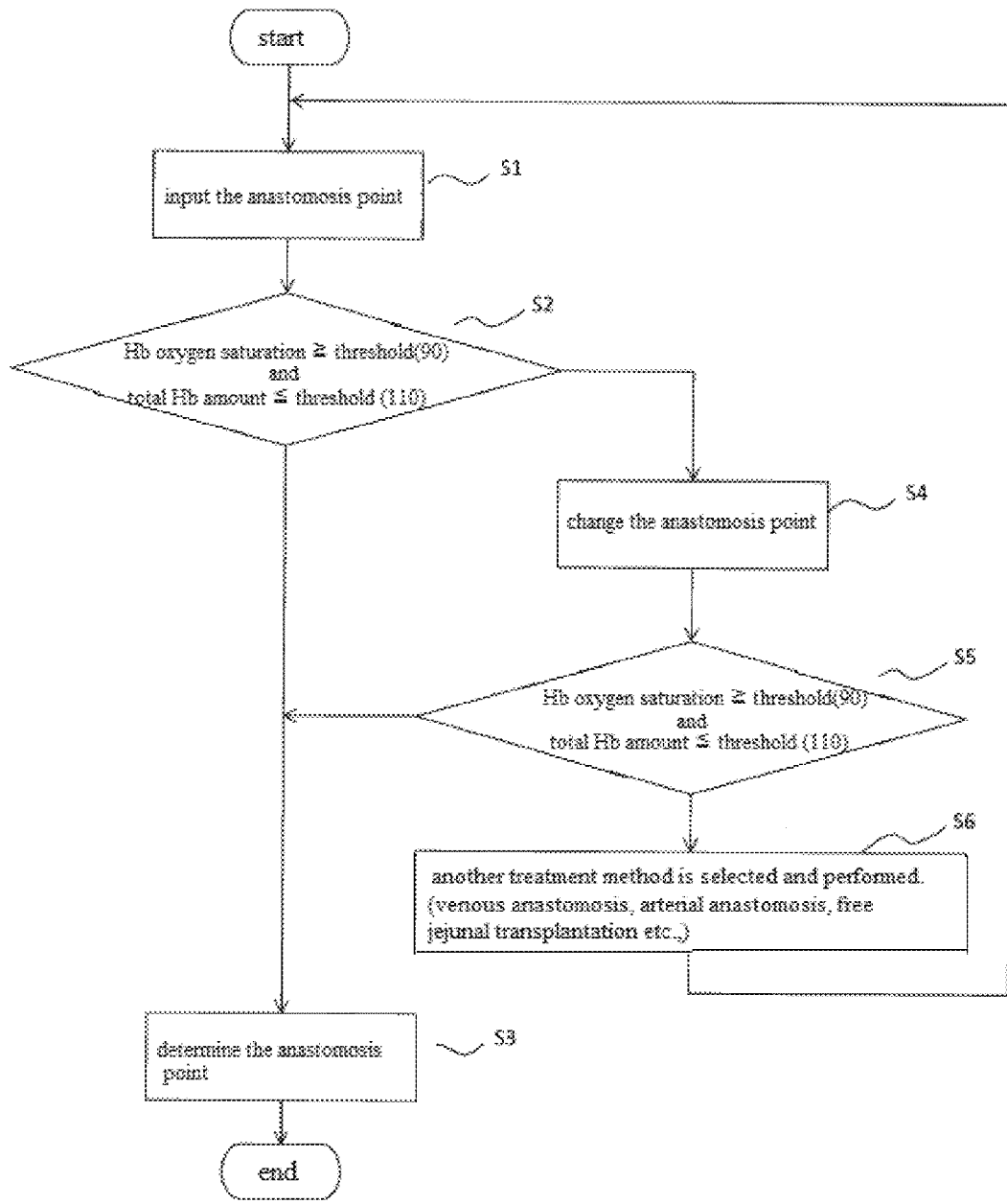
FIG. 13 is a flowchart showing the operation of the treatment support apparatus according to the third embodiment.

FIG. 12 is a functional block diagram showing the configuration of the treatment support apparatus according to the present embodiment. Here, in the treatment support apparatus according to the present embodiment, it is assumed that an image is generated from the light component of the hemoglobin oxygen saturation calculated by the oxygen saturation calculation unit 7 and the light component of the total hemoglobin amount calculated by the hemoglobin amount calculation unit 8 by the image generation unit 9 shown in FIG. 2 as a premise, and the processing is started in a state in which the generated image of the hemoglobin oxygen saturation and the total hemoglobin amount image are displayed on the display b.

The treatment support apparatus 120 includes, an input unit 121 for inputting anastomosis position information a input based on an operation of a user on a display b displayed in a state in which the hemoglobin oxygen saturation and the total hemoglobin amount are visually recognizable by an image, a storage unit 122 for inputting and storing the hemoglobin oxygen saturation and the total hemoglobin amount determined to be suitable for anastomosis as thresholds from the input unit 121 in advance, and storing other setting values and information necessary for processing, a determination unit 123 for comparing the hemoglobin oxygen saturation and the total hemoglobin amount at the input anastomosis position with the threshold stored in the storage unit 122 to determine whether the hemoglobin oxygen saturation and the total hemoglobin amount at the input anastomosis position are suitable for anastomosis and an output control unit 124 for outputting the determination result of the determination unit 123 to the display b.

Actual experimental results will be described in detail in the examples. The user first inputs, as anastomosis site information, a site judged to be suitable for anastomosis on the display b with respect to an image generated by the hemoglobin quantifying apparatus. Then, when the hemoglobin oxygen saturation at the input anastomosis site is higher than the predetermined threshold stored in the storage unit 122 and the total hemoglobin amount is lower than the predetermined threshold stored in the storage unit 122, the determination unit 123 determines the input site as the anastomosis site.

When the hemoglobin oxygen saturation at the input anastomosis site is equal to or less than the predetermined threshold stored in the storage unit 122 or the total hemoglobin amount is equal to or more than the predetermined threshold stored in the storage unit 122, the output control unit 124 presents the fact to input another anastomosis site. The user inputs another place physically anastomosable, and the determination unit 123 performs the same processing as described above again, thereby determining whether the anastomosis is appropriate at that place. As a result, if the anastomosis is appropriate, the changed input location is determined as the anastomosis location.

The above process is repeated as long as other anastomotic sites can be entered. Then, when another anastomosis point cannot be input (i.e., when the user inputs a message indicating that the anastomosis point cannot be input), the determination unit 123 presents and outputs another treatment method stored in the storage unit 122. The user selects the outputted treatment method, and after the treatment method is performed, the hemoglobin oxygen saturation and the total hemoglobin amount are again obtained to specify the anastomosis site.

In the present embodiment, the hemoglobin oxygen saturation and the total hemoglobin amount at the anastomosis site input by the user may be stored in the storage unit 122 in association with the image in advance, or may be calculated and obtained in real time in accordance with the operation of the user.

In addition, the storage unit 122 may store setting values, thresholds, and other information necessary for processing for each treatment site (e.g., various organs of the entire body including the esophagus, stomach, liver, small intestine, and large intestine) in advance, and when the user first inputs the treatment site, the setting values, thresholds, etc. corresponding to the treatment site may be read out, and processing suitable for the treatment site may be performed.

Next, the operation of the treatment support apparatus according to the present embodiment will be described. FIG. 13 is a flowchart showing the operation of the treatment support apparatus according to the present embodiment. Here, the process of determining the anastomosis site when anastomosing the esophagus and the gastric tube will be described.

First, in a state where an image generated from the light component of the hemoglobin oxygen saturation and the light component of the total hemoglobin amount is displayed on the display b, the anastomosis site is input to the input unit 121 as anastomosis site information a in accordance with an instruction from the user (S). The determination unit 123 reads the threshold value of the hemoglobin oxygen saturation and the threshold value of the total hemoglobin amount stored in the storage unit 122, and determines whether the hemoglobin oxygen saturation of the anastomosis site inputted to the input unit 121 is equal to or greater than the threshold value (e.g., 90) and the total hemoglobin amount is equal to or less than the threshold value (e.g., 110) (S2). When the condition is satisfied, the input anastomotic site is determined as the anastomotic site(S3), and the output control unit 124 displays the fact on the display b. At this time, the fact that the anastomosis point has been determined may be actively displayed on the display b, or the fact that information such as an alert is not displayed may be made to indicate that the anastomosis point has been determined.

When the anastomosis site inputted to the input unit 121 does not satisfy the condition of step S2, the user changes the anastomosis site on the display b in step S4 and inputs other anastomosis site information a to the input unit 121. With respect to the changed anastomosis site information a of the anastomosis site, the determination unit 123 again determines whether the hemoglobin oxygen saturation is equal to or higher than a threshold (e.g., 90) and the total hemoglobin amount is equal to or lower than a threshold (e.g., 110) (S5). When the condition is satisfied, the changed anastomosis site is determined as the anastomosis site in step S3, and the output control unit 124 displays the fact on the display b.

If the condition is not satisfied, another treatment method is selected and performed (S6). Other methods of operation include, for example, free jejunal transplantation in which the free jejunum is interposed between the esophagus and the gastric tube (at this time, the free jejunal artery and the vein are also anastomosed to the blood vessel of the neck), venous anastomosis in which the vein of the gastric tube and the vein of the neck are anastomosed when the venous return of the gastric tube is judged to be poor, and arterial anastomosis in which the artery of the gastric tube and the artery of the neck are anastomosed when the arterial blood flow of the gastric tube is judged to be impaired.

When these treatment methods are stored in the storage unit 122 in advance and the condition of step S5 is not satisfied, the output control unit 124 reads out the information on the other treatment methods from the storage unit 122 and displays the information on the display b. The user selects any one or a plurality of combinations from these treatment methods, and actually performs the treatment.

As a result of the operation, the process returns to step S again to input the anastomosis site, and the above-described processes are repeated to specify the anastomosis site.

As described above, in the treatment support apparatus according to the present embodiment, since the image is generated from the light component of the hemoglobin amount, the image is generated based on the light component of the oxygen saturation of the hemoglobin, the generated respective images are displayed on the display, the anastomosis point in the displayed image is specified based on the operation of the user, and the anastomosis possibility is judged based on the hemoglobin amount and the oxygen saturation of the hemoglobin at the specified anastomosis point, it is possible to objectively present and judge the position suitable as the anastomosis point not only by the judgment of the user (physician), but also as a numerical value. The calculation of the hemoglobin amount and the hemoglobin oxygen saturation makes it possible to evaluate the blood flow of organs, to diagnose tumors and determine the invasion range, to diagnose the degree and range of inflammation, etc. in addition to the possibility of anastomosis.

Examples

The following clinical tests were conducted using the hemoglobin quantifying apparatus and the treatment support apparatus according to the present invention. The operation site was the esophagus and gastric tube. It was clarified that the hemoglobin quantifying apparatus and the t treatment support apparatus ere very effective for the anastomosis of the esophagus and gastric tube in order to specify the anastomosis site.

Four typical cases are described below.

(1) Circulation Type

Figure 14:
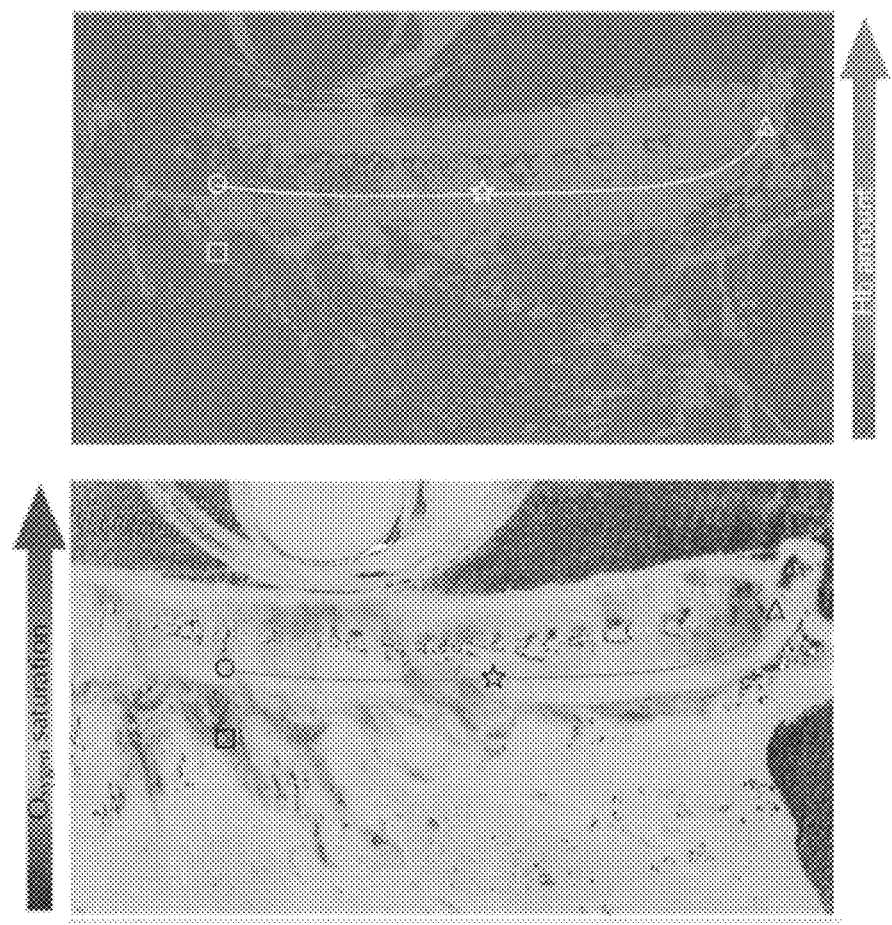
FIG. 14 is a diagram showing an image of a circulation type case in the embodiment.

FIG. 14 is a diagram showing an image of a circulation type case. This is a case in which the hemoglobin oxygen saturation is 90 or more up to the distal end of the gastric tube (left image), and the total hemoglobin amount is kept constant up to the distal end (right image). The location of C1 (□ marker) is an artery, and the hemoglobin oxygen saturation and total hemoglobin amount at the three locations of C2 (○ marker), A (☆marker), and E (Δmarker) are shown with the hemoglobin oxygen saturation and total hemoglobin amount at the location of C1 being 100. In this circulation type, hemoglobin oxygen saturation and total hemoglobin content are high at all points, and it is judged that anastomosis is possible without any problem at all points.

(2) Ischemic Type

Figure 15:
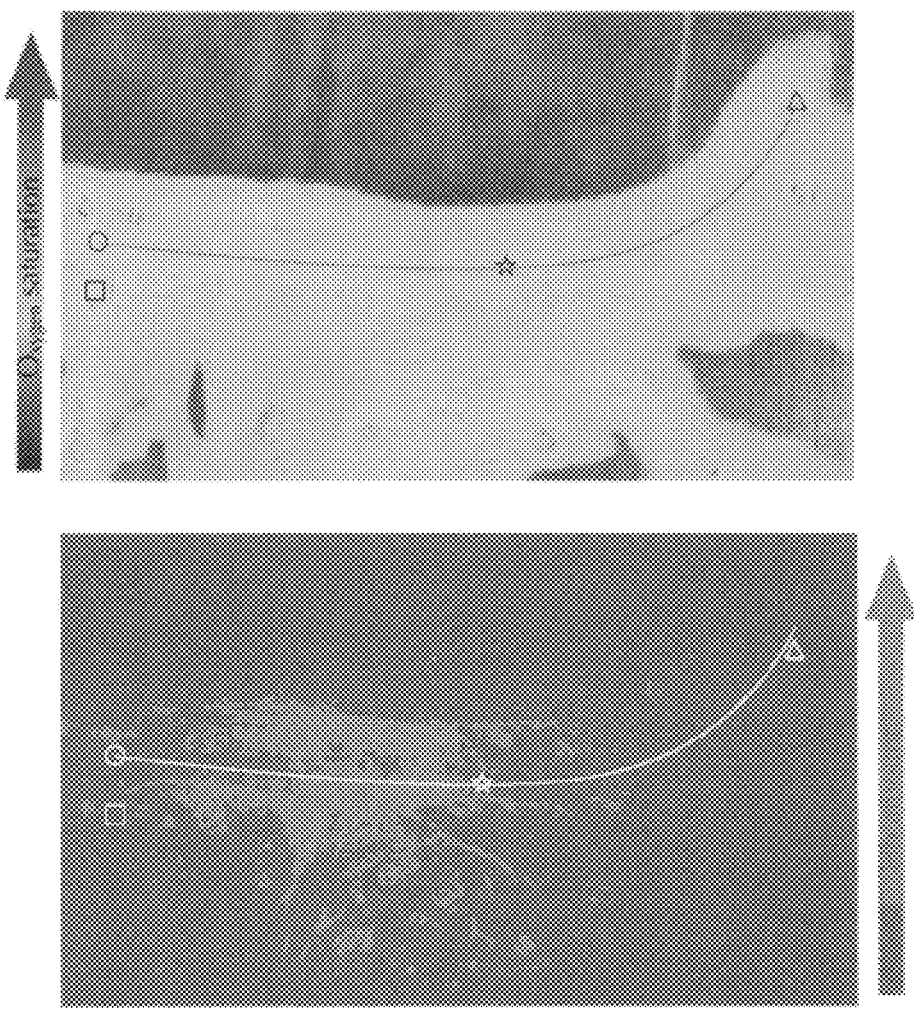
FIG. 15 is a diagram showing an image of an ischemic type case in the embodiment.

FIG. 15 is a diagram showing an image of an ischemic type case. This is the case in which the hemoglobin oxygen saturation of the left image is lower in the central portion of the gastric tube and lower in the distal portion, and the total hemoglobin amount of the right image is higher in the central portion of the gastric tube and lower in the distal portion. It is also judged that there is a disorder in the continuity of the artery and vein with the distal end. The location of C1 (□ marker) is an artery, and the hemoglobin oxygen saturation and total hemoglobin amount at the three locations of C2 (○ marker), A (■ marker), and E (Δ marker) are shown with the hemoglobin oxygen saturation and total hemoglobin amount at the location of C1 being 100. In this case, anastomosis was performed at site A, but hemoglobin oxygen saturation at that site was 83.1 and total hemoglobin was 125.2, and anastomotic stenosis was complicated after the operation.

(3) Congestion Type

Figure 16:
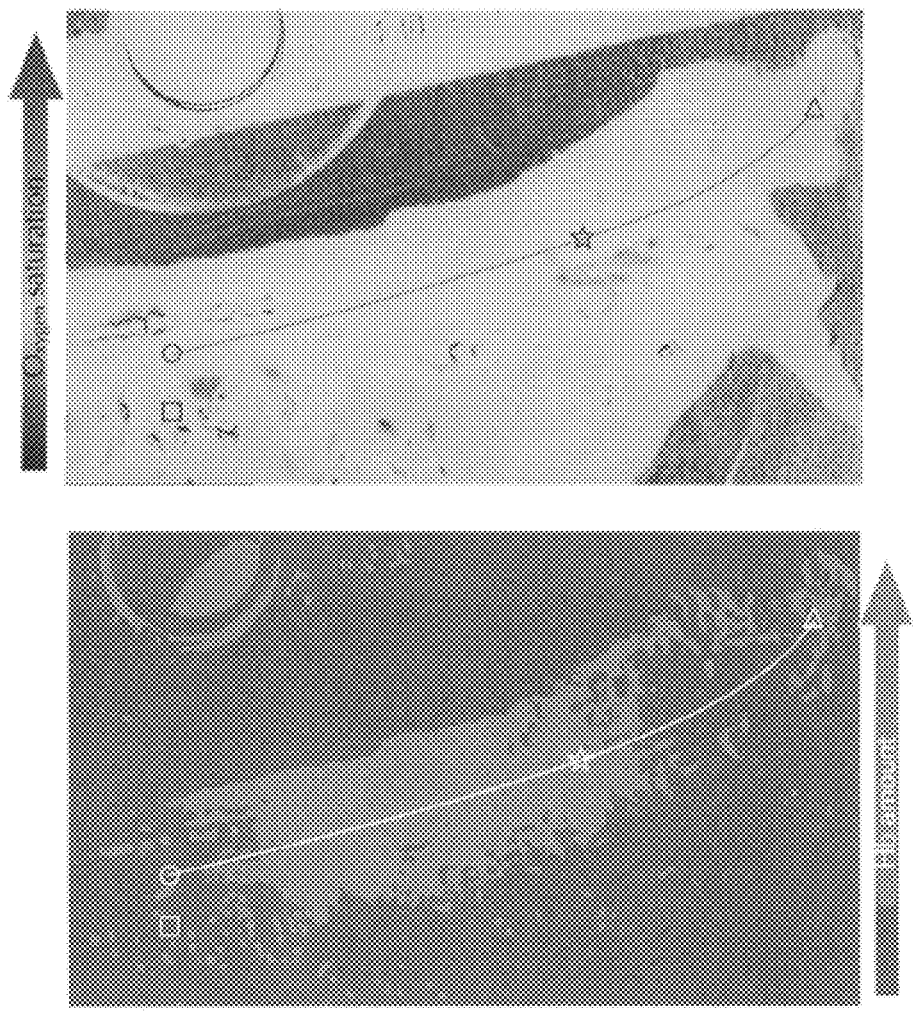
FIG. 16 is a diagram showing an image of a congestion type case in the embodiment.

FIG. 16 is a diagram showing an image of a congestion type case. In this case, the hemoglobin oxygen saturation in the central part of the gastric tube is low (left image) and the total hemoglobin amount is high (right image). In addition, the terminal portion has high hemoglobin oxygen saturation, the total hemoglobin amount tends to decrease, and it is judged that the continuity of the artery and vein with the terminal is not impaired. In this case, the anastomosis was performed at the site A (distal to the central portion of the gastric tube), but no problem occurred in the anastomosis.

(4) Mixed Type

Figure 17:
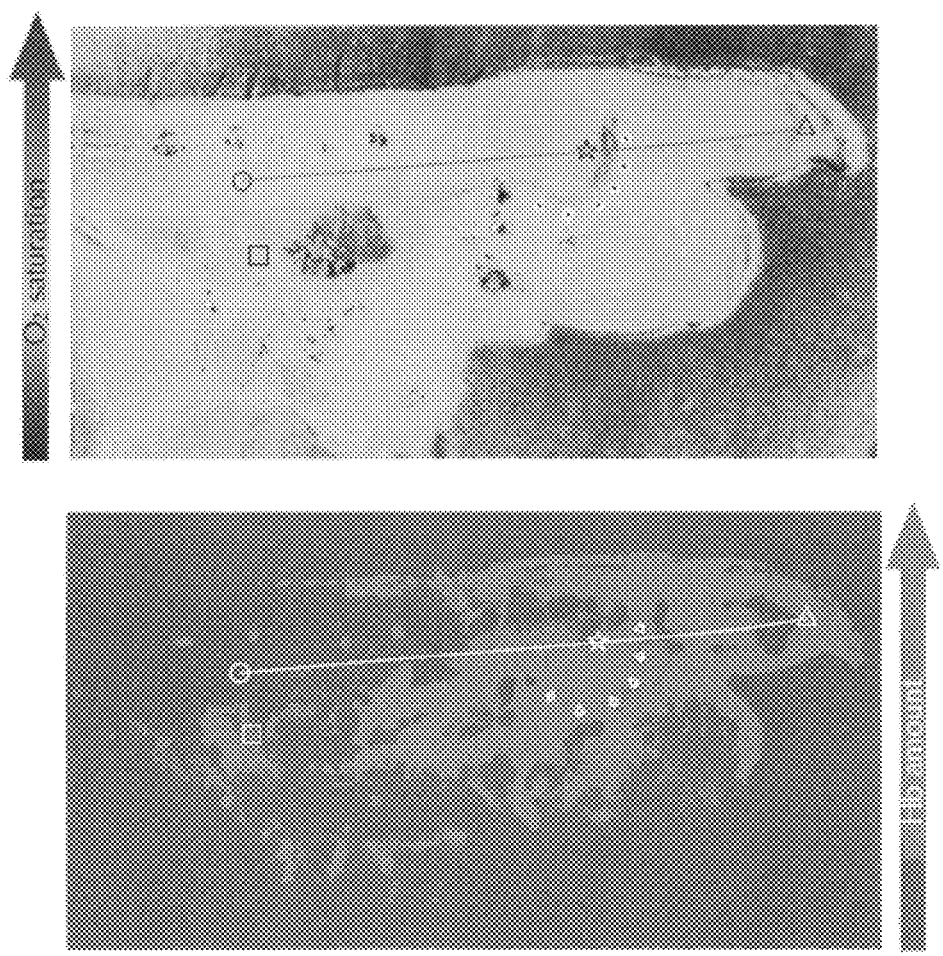
FIG. 17 shows an image of a mixed case in the embodiment.

FIG. 17 is a diagram showing an image of a mixed type case. Also in FIG. 17, the point of C1 (□ marker) is an artery, and the hemoglobin oxygen saturation and the total hemoglobin amount at three points of C2 (○ marker), A (■ marker) and E (Δ marker) are shown with the hemoglobin oxygen saturation and the total hemoglobin amount at the location of C1 being 100. Here, a decrease in hemoglobin oxygen saturation from the point of C2 to the end is observed, and an increase in total hemoglobin amount is observed. The anastomosis site was site A. The hemoglobin oxygen saturation was extremely low (62.4) in the peripheral portion of the anastomosis site. The linear portion in which the total hemoglobin level was high (144.4) was observed. Intravenous thrombosis was observed. Venous anastomosis of the internal jugular vein and the omental vein was performed after the anastomosis, and anastomotic failure developed after the operation.

Figure 18:
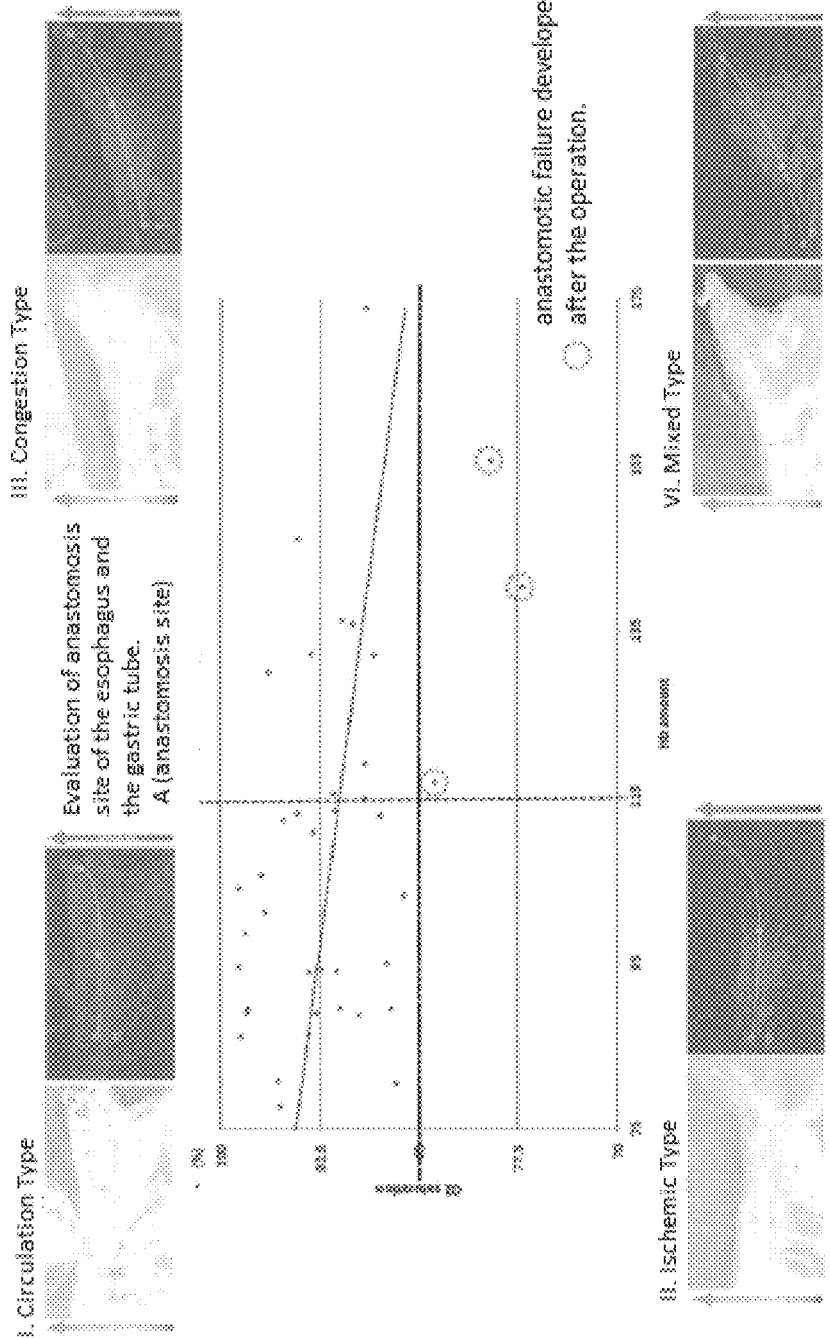
FIG. 18 is a diagram showing the results of classifying a plurality of cases in the embodiment.

A plurality of cases were classified on the basis of the above four typical cases. The results are shown in FIG. 18. FIG. 18 is a plot of hemoglobin oxygen saturation and total hemoglobin level at the site of anastomosis. Three cases indicated by the broken line developed failure of the sutures after the operation, and the progress was steady in the other cases.

From the result of FIG. 18, it can be judged that, in the procedure in the case of anastomosis between the esophagus and the gastric tube, when the hemoglobin oxygen saturation is 85 or less and the total hemoglobin amount is 115 or more, there is a possibility that failure of the sutures may occur after the operation. Therefore, it is possible to perform safe and low-risk procedures based on these judgment materials when identifying the anastomosis site before surgery.

In this embodiment, the anastomosis between the esophagus and the gastric tube was subjected to a clinical test, but by carrying out clinical tests in the same manner in other procedures, it becomes possible to set numerical values according to the procedure method and the object of the procedure.

In each of the above embodiments and the present embodiment, the hemoglobin oxygen saturation and the total hemoglobin amount at the treatment site are respectively determined based on the hemoglobin oxygen saturation and the total hemoglobin amount in the artery (in the present embodiment, the reference value is 100), however, for example, the hemoglobin oxygen saturation and the total hemoglobin amount at the treatment site can be determined based on the bronchial artery in the case of the lung and the portal vein in the case of the liver because the hepatic artery is small.

EXPLANATION OF CODES

1 Hemoglobin quantifying apparatus
2 Light receiver unit
3 First wavelength component acquisition unit
4 Second wavelength component acquisition unit
5 G component acquisition unit
6 B component acquisition unit
7 Oxygen saturation calculation unit
8 Hemoglobin amount calculation unit
9 Image generation unit
10 Display control unit
100 Computer
101 CPU
102 RAM
103 ROM
104 Hard-disk
105 Communication I/F
106 input/output I/F

The invention claimed is:

1. A hemoglobin quantifying apparatus comprising:
a component acquiring means for acquiring components identified by any two narrow wavelength bands having different reflection characteristics according to an oxygen saturation of hemoglobin and a white component, which are reflected light from a biological tissue, and
a hemoglobin amount calculating means for calculating the hemoglobin amount based on first and second narrow wavelength bands light components,
wherein the hemoglobin amount calculating means corrects the hemoglobin amount calculated based on the first and second narrow wavelength band light components, based on a blue component and a green component to calculate the hemoglobin amount.

2. The hemoglobin quantifying apparatus according to claim 1, further comprising an oxygen saturation calculating means for calculating the oxygen saturation of the hemoglobin based on a ratio of the first and second narrow wavelength band light components.

3. The hemoglobin quantifying apparatus according to claim 2, wherein the oxygen saturation calculating means calculates the oxygen saturation based on the oxygen saturation of the artery.

4. The hemoglobin quantitation apparatus according to claim 2, further comprising a display control means for switching between displaying the hemoglobin amount calculated by the hemoglobin amount calculating means and the oxygen saturation calculated by the oxygen saturation calculating means.

5. A treatment support apparatus using the hemoglobin quantifying apparatus according to claim 2, comprising:
a first image generating means for generating an image from a light component of the hemoglobin amount calculated by the hemoglobin amount calculating means;
a second image generating means for generating an image based on a light component of the oxygen saturation of hemoglobin calculated by the oxygen saturation calculating means;
a display control means for displaying each generated image on a display;
an anastomosis site specifying means for specifying an anastomosis site in the displayed image based on an operation of a user; and
a determining means for determining whether an anastomosis is permitted based on the hemoglobin amount and the oxygen saturation of hemoglobin in the specified anastomosis site.

6. The hemoglobin quantifying apparatus according to claim 1, wherein the hemoglobin amount calculating means calculates the amount of hemoglobin as a light component indicating the amount of hemoglobin by dividing a sum value of the light the first and second narrow wavelength band light components by the blue component and the green component.

7. A treatment support apparatus using the hemoglobin quantifying apparatus according to claim 5, comprising:
a first image generating means for generating an image from a light component of the hemoglobin amount calculated by the hemoglobin amount calculating means;

a second image generating means for generating an image based on a light component of the oxygen saturation of hemoglobin calculated by the oxygen saturation calculating means;

a display control means for displaying each generated image on a display;

an anastomosis site specifying means for specifying an anastomosis site in the displayed image based on an operation of a user; and a determining means for determining whether an anastomosis is permitted based on the hemoglobin amount and the oxygen saturation of hemoglobin in the specified anastomosis site.

8. A hemoglobin quantitation method, comprising:

a component acquisition step for acquiring components by any two narrow wavelength bands having different reflection characteristics different according to the oxygen saturation of hemoglobin and a white component, which are reflected light from biological tissue, and a hemoglobin amount calculation step for calculating the hemoglobin amount based on first and second narrow wavelength band light components, wherein the hemoglobin amount calculation step corrects the hemoglobin amount calculated based on the first and second narrow wavelength band light components based on a blue component and a green component.

9. A non-transitory computer readable medium storing a hemoglobin quantitation program which causes a computer to execute steps comprising:

a step of acquiring first and second narrow wavelength band light components identified by two narrow wavelength bands having different reflection characteristics according to oxygen saturation of hemoglobin and a white component, which are reflected light from a biological tissue, and a step of calculating a hemoglobin amount based on the first and second narrow wavelength band light components, wherein in the step of calculating the hemoglobin amount, the hemoglobin amount calculated based on the first and second narrow wavelength band light components is corrected based on a blue component and a green component to calculate the hemoglobin amount.

\* \* \* \* \*